(12) United States Patent
Kameyama

(10) Patent No.: US 8,190,434 B2
(45) Date of Patent: May 29, 2012

(54) APPARATUS FOR PROVIDING INFORMATION FOR VEHICLE

(75) Inventor: Shogo Kameyama, Chiryu (JP)

(73) Assignee: Denso Corporation, Kariya (JP)

( * ) Notice: Subject to any disclaimer, the term of this patent is extended or adjusted under 35 U.S.C. 154(b) by 470 days.

(21) Appl. No.: 12/476,421

(22) Filed: Jun. 2, 2009

(65) Prior Publication Data

US 2009/0318777 A1 Dec. 24, 2009

(30) Foreign Application Priority Data

Jun. 3, 2008 (JP) ................................ 2008-146123

(51) Int. Cl.
*G10L 21/06* (2006.01)
(52) U.S. Cl. ...................................................... 704/270
(58) Field of Classification Search .................. 704/270
See application file for complete search history.

(56) References Cited

U.S. PATENT DOCUMENTS

| | | | |
|---|---|---|---|
| 7,343,234 B2 * | 3/2008 | Kameyama | 701/36 |
| 7,821,382 B2 * | 10/2010 | Kameyama | 340/425.5 |
| 8,090,367 B2 * | 1/2012 | Kameyama | 455/426.1 |
| 2002/0188455 A1 | 12/2002 | Shioda et al. | |
| 2007/0192038 A1 | 8/2007 | Kameyama | |
| 2007/0299911 A1 | 12/2007 | Mizunashi et al. | |
| 2009/0292528 A1 * | 11/2009 | Kameyama | 704/9 |

FOREIGN PATENT DOCUMENTS

| | | |
|---|---|---|
| JP | 06-315572 | 11/1994 |
| JP | 09-231227 | 9/1997 |
| JP | 10-177468 | 6/1998 |
| JP | 2000-268047 | 9/2000 |
| JP | 2001-256036 | 9/2001 |
| JP | 2002-366166 | 12/2002 |
| JP | 2003-030234 | 1/2003 |
| JP | 2003-186897 | 7/2003 |
| JP | 2004-338496 | 12/2004 |
| JP | 2005-275601 | 10/2005 |
| JP | 2006-055406 | 3/2006 |
| JP | 2006-092430 | 4/2006 |
| JP | 2006-282111 | 10/2006 |
| JP | 2007-212421 | 8/2007 |

OTHER PUBLICATIONS

Japanese Office Action dated Apr. 15, 2010, issued in corresponding Japanese Application No. 2008-146123, with English translation.
Press Release, Mar. 3, 2006 of NEC Corporation, NEC Design Ltd., SGI Japan, "NEC, Design & SGI Collaboratively Develop "KOTOHANA"", http://www.sgi.co.jp/newsroom/press_releases/2006/mar/kotohana_e.html., 6 pages.

* cited by examiner

*Primary Examiner* — Susan McFadden
(74) *Attorney, Agent, or Firm* — Nixon & Vanderhye P.C.

(57) ABSTRACT

The apparatus detects a mental condition of a user when a conversation content is inputted. The apparatus further collects service information based on a keyword extracted from conversation and a detected mental condition. For example, a user's interest is determined by considering a mental condition, i.e., a user's feeling, when the conversation containing the keyword is held. For example, the apparatus provides information collected based on the keyword which the user expresses a good feeling. As a result, it is possible to collect information reflecting the user's interest and hobby more exactly from a user's conversation in the vehicle. It is possible to provide the apparatus for providing information for vehicles which can respond to a variety of user tastes.

15 Claims, 28 Drawing Sheets

| DATE | USER | DESTINATION | CLASS | FREQUENCY |
|---|---|---|---|---|
| 2003.3.1 | MOTHER | SHOP A | NJC2 | 2 |
| 2003.3.1 | MOTHER | RESTAURANT A | NJC1 | 1 |
| 2003.3.2 | FATHER | RESTAURANT B | NJC1 | 8 |
| 2003.3.8 | FATHER | RESTAURANT C | NJC1 | 2 |
| ⋮ | ⋮ | ⋮ | ⋮ | ⋮ |
| 2003.8.3 | ALL FAMILY | SEASHORE A | NJC3 | 1 |
| 2003.8.3 | ALL FAMILY | RESTAURANT D | NJC1 | 1 |
| ⋮ | ⋮ | ⋮ | ⋮ | ⋮ |

| | |
|---|---|
| (TAKASHI) | It is "December" +1.  Where do you want to go this year? |
| (HITOMI) | I like "skiing" +1.  I could not go "last year" 0. |
| (TAKASHI) | I want to go "skiing" +1.  When did we go last time? |
| (HITOMI) | We went to "DOKAYUKI plateau" +1 in "February" +1 "before last." +1<br>I was tired since we took a "bus" -1 trip. |
| (TAKASHI) | Yah, We took a "bus" 0 trip.  It took 5 hours.<br>The road was narrow.  The "rest time" 0 was too long.<br>I would never take a "bus" -1. |
| (HITOMI) | Can I go by the "car" +1 "this year?" +1 |
| (TAKASHI) | We should replace to "stud-less" +1 "tires" +1<br>for "snow" +1 driving. |
| (HITOMI) | By the way, a "TV" +1 show said that<br>it seems to be an enough "snow" +1.<br>Do you think I can drive even in a "snow?" +1<br>if we replace the "tires." +1 |
| (TAKASHI) | There are many kinds of "stud-less" +1 "tires" +1,<br>so we shall replace to a good one. |
| (HITOMI) | Why don't we replace it today.<br>It would be hard, if it is "snow" +1<br>even in the around here,<br>since I must pick up and drop the child. |
| (TAKASHI) | Would you like to visit any store? |
| (HITOMI) | Do you know any store selling "tires" +1 near here? |
| (TAKASHI) | "Search." |

FIG. 14

| USER NAME | WORD | MENTAL POINT |
|---|---|---|
| TAKASHI | DECEMBER | +1 |
| HITOMI | SKIING | +1 |
| HITOMI | LAST YEAR | 0 |
| TAKASHI | SKIING | +1 |
| HITOMI | BEFORE LAST | 0 |
| HITOMI | FEBRUARY | +1 |
| HITOMI | DOKAYUKI PLATEAU | +1 |
| HITOMI | BUS | −1 |
| TAKASHI | BUS | 0 |
| TAKASHI | BUS | −1 |
| HITOMI | THIS YEAR | +1 |
| HITOMI | CAR | +1 |
| TAKASHI | SNOW | −1 |
| TAKASHI | STUD-LESS | +1 |
| TAKASHI | TIRE | +1 |
| HITOMI | TV | +1 |
| HITOMI | SNOW | +1 |
| HITOMI | TIRE | +1 |
| HITOMI | SNOW | +1 |
| TAKASHI | STUD-LESS | +1 |
| TAKASHI | TIRE | +1 |
| HITOMI | SNOW | +1 |
| HITOMI | CHILD | 0 |
| TAKASHI | STORE | 0 |
| HITOMI | TIRE | +1 |

FIG. 15

| WORD | TOTALED POINT |
|---|---|
| DECEMBER | +1 |
| SKIING | +2 |
| LAST YEAR | +1 |
| BEFORE LAST | 0 |
| FEBRUARY | +1 |
| DOKAYUKI PLATEAU | +1 |
| BUS | -2 |
| THIS YEAR | +1 |
| CAR | +1 |
| TIRE | +4 |
| STUD-LESS | +2 |
| TV | +1 |
| SNOW | +4 |
| CHILD | 0 |
| STORE | 0 |

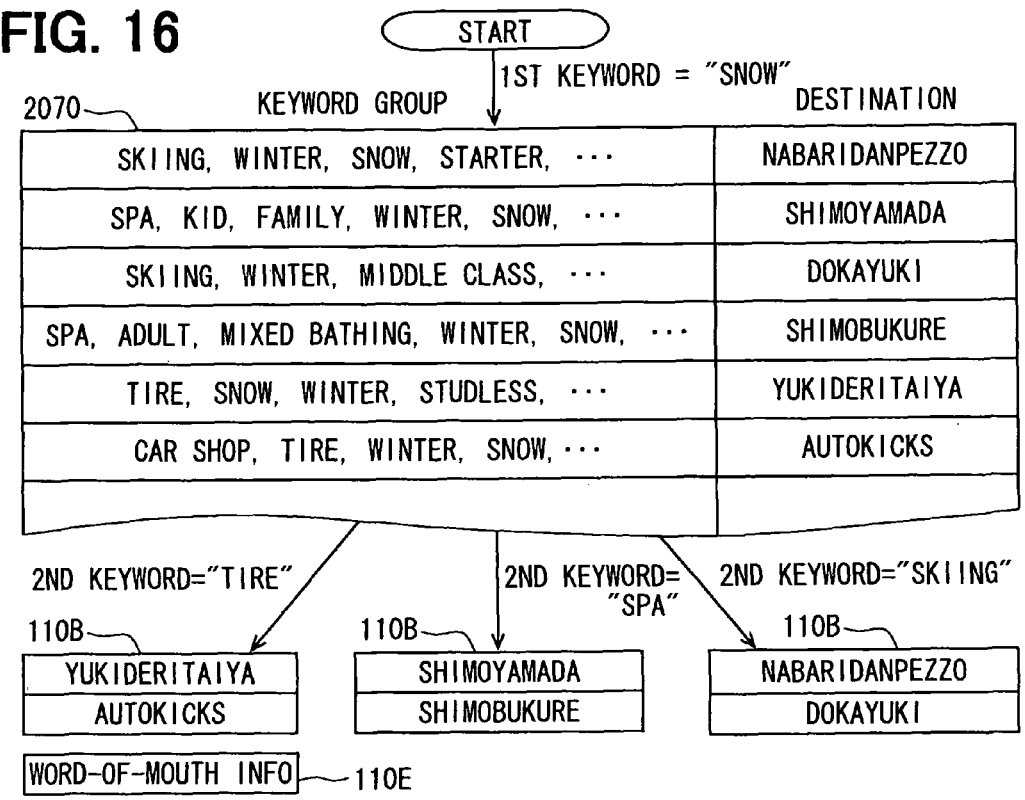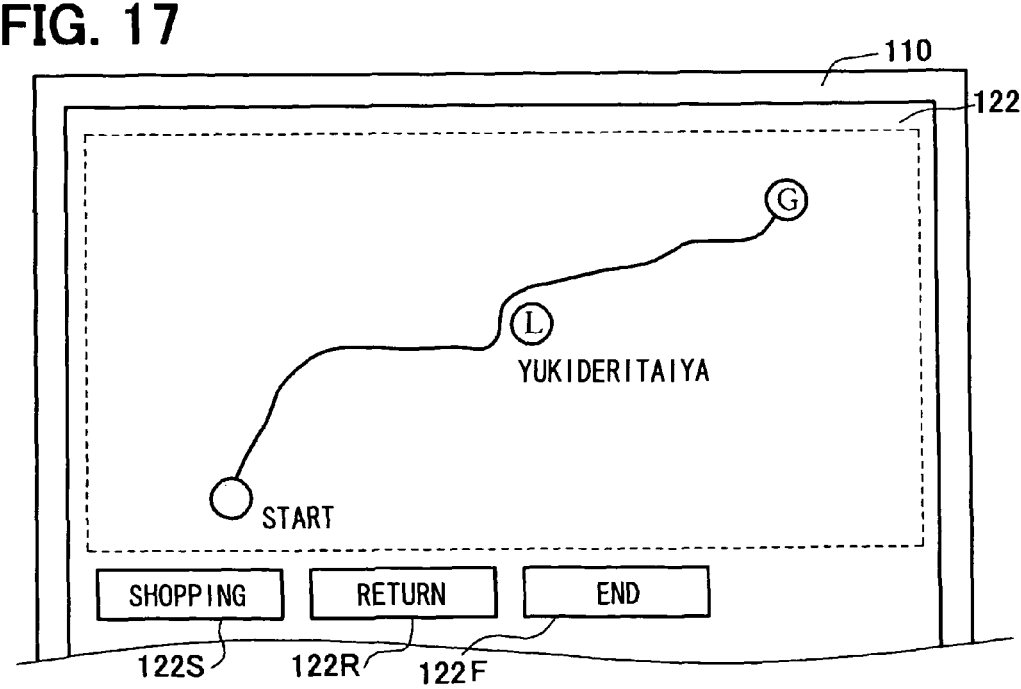

FIG. 24

(SHOUGO) Let us hit the road! Go!
(YUKIO) What road are you going to take to "ITO?" +1
(SHOUGO) Well, we can use the "toll road" +1 to "NUMAZU." +1
(YUKIO) There is a significant distance from "NUMAZU" 0 to "ITO" 0, isn't it?
(SHOUGO) About 50 kilo-meters drive.
Because we must take a "non-toll road" +1, it will usually take 2 hours to "NUMAZU" +1.
But, it seems "jammed" 0 today, I guess that
it would take about the same from there to "ITO" 0 in a worst scenario.
(ERIKA) What? It takes 2 hours in a "non-toll road?" -1 It must be tired.
(SHOUGO) Don't you love the "sea" 0, do you?
(ERIKA) Not so much. I don't want to visit "ITO" -1 so seriously.
(YUKIO) Do you give up going to "ITO?" -1
(SHOUGO) How about visiting an area of "Fuji five lakes" +1 through "GOTENBA?" +1
It is fine today, so that we may be able to see "Mt. Fuji" +1 clearly.
(YUKIO) "Fuji five lakes" +1, that sounds good.
(SHOUGO) It would be just about 10 kilo-meters drive on a national high class road
from the interchange of "GOTENBA" +1, and
only 15 kilo-meters drive on the road of "Fuji file lakes" +1
from "SUBASHIRI." +1 to the "lake KAWAGUCHI." +1
(ERIKA) Is it shorter than "ITO?" 0
(SHOUGO) We only need 20 minutes drive on a "non-toll road." 0
Remains are all "toll roads." 0
We can arrive there about 1 hour from "NUMAZU" 0 if it is smooth.
(ERIKA) Oh. That sounds great. I want to see "Mt. Fuji." +2
(SHOUGO) "Search"

(Activate the contents)
It is known as the one of the Five Lakes of Mount Fuji where you can overlook Mt. Fuji.
There are art museums, hotels, hot springs, parks, etc. around the lake.
You can enjoy fishing, a canoeing, a sight seeing boat, etc. in this leisure spot with rich nature.

FIG. 25

| USER NAME | WORD | MENTAL POINT |
|---|---|---|
| YUKIO | ITO | +1 |
| SHOUGO | TOLL ROAD | +1 |
| SHOUGO | NUMAZU | 0 |
| YUKIO | NUMAZU | 0 |
| YUKIO | ITO | 0 |
| SHOUGO | NON-TOLL ROAD | +1 |
| SHOUGO | NUMAZU | +1 |
| SHOUGO | IZU | 0 |
| SHOUGO | ITO | 0 |
| ERIKA | NON-TOLL ROAD | -1 |
| SHOUGO | SEA | 0 |
| ERIKA | ITO | -1 |
| YUKIO | ITO | -1 |
| SHOUGO | GOTENBA | +1 |
| SHOUGO | FUJI FIVE LAKES | +1 |
| SHOUGO | Mt. FUJI | +1 |
| YUKIO | Mt. FUJI | +1 |
| SHOUGO | SUBASHIRI | +1 |
| SHOUGO | FUJI FIVE LAKES | +1 |
| SHOUGO | LAKE KAWAGUCHI | +1 |
| ERIKA | ITO | 0 |
| SHOUGO | NON-TOLL ROAD | 0 |
| SHOUGO | TOLL ROAD | +1 |
| SHOUGO | NUMAZU | 0 |
| ERIKA | Mt. FUJI | +2 |

| ITO | -1 |
|---|---|
| KOUSOKU | +2 |
| NUMAZU | +1 |
| NON-TOLL ROAD | 0 |
| IZU | 0 |
| SEA | 0 |
| GOTENBA | +1 |
| FUJI FIVE LAKES | +2 |
| Mt. FUJI | +4 |
| SUBASHIRI | +1 |
| LAKE KAWAGUCHI | +1 |

FIG. 28

```
(DORAO)    I am really getting "hungry" +1.
(HIGEJI)   Well, do you think that "TENKOMORI" +1 is near here?
(MASUTA)   "TENKOMORI" +1 is advertising on "TV" +1 programs, isn't it?
           Ah, let me see.
(HIGEJI)   I know that it is famous for a thick "roast pork" +1.
(SHOUGO)   I like a "roast pork" +2 very much!
           Hey, where is "TENKOMORI" +2. Let us go! Go!
(DORAO)    Do you want to have a "noodle" 0 again?
           SHOUGO really loves a "roast pork", doesn't he?
(MASUTA)   You are the No.1 "roast pork" +1 freak in this group.
(HIGEJI)   He is called as a "roast pork" +1 king.
(SHOUGO)   Shut up! Nothing bad for loving "roast pork." +2
           You all must have "roast pork" +2 too. Okay?
(DORAO)    No help. What do you think, MASUTA and HIGEJI?
(MASUTA)   I am Okay with a "roast pork" +1.
(HIGEJI)   I am Okay with a "roast pork" +1 too.

(Activate the contents) (With an image song of "TENKOMORI.")
           It is famous for a thick roast pork!
           "TENKOMORI" good for today.
           The nearby store is on the screen.
```

FIG. 29

| WORD | TOTALED POINT |
|---|---|
| HUNGRY | +1 |
| TENKOMORI | +4 |
| TV | +1 |
| ROAST PORK | +10 |

APPARATUS FOR PROVIDING INFORMATION FOR VEHICLE

CROSS REFERENCE TO RELATED APPLICATION

This application is based on Japanese Patent Application No. 2008-146123 filed on Jun. 3, 2008, the contents of which are incorporated herein by reference in its entirety.

FIELD OF THE INVENTION

This invention relates to an apparatus for providing information for vehicles.

BACKGROUND OF THE INVENTION

In this art of technology, the following prior documents are known.
Patent document 1: JP-2003-30234-A
Patent document 2: JP-2008-5175-A The patent document 1 discloses a technology that conducts a morphological analysis for a natural language sentence which is in an in-company e-mail in a company or is inputted or spoken by a user of an extension telephone line, and determines a user's personal interest based on an occurrence frequency of keywords in the sentence. The patent documents 2 discloses a technology that conducts a morphological analysis after converting a speech of a conference participant, and determining a degree of interest to conference information based on a occurrence frequency of keywords contained. The above-mentioned technology for analyzing a content of speech of a user, and determining interest information based on a frequency of a word may be applied also to an information providing apparatus for vehicle such as a car. For example, it is possible to search and output appropriate information by determining an interest object of a user based on an occurrence frequency of a keyword which is recognized by a speech recognition performed on a in-car speech of crews in a vehicle. For example, the information is a destination as a guidance object for a car-navigation system, information content, etc.

SUMMARY OF THE INVENTION

Subjects of the technologies in the patent documents 1 and 2 are conversations in companies or conventions. Such conversations are usually oriented toward an in-company matter, and are stereotype or business like. Therefore, information indicative of an interest reflecting a personal feeling is rarely extracted. However, in case of an in-car conversation, except for a vehicle used for a commercial purpose, conversations usually contains private matters among familiar persons. Therefore, such a conversation has a tendency which easily reflects a personal feeling including joy, anger, humor and pathos in a deeply manner. In such a case, it is concerned that it is easily generate errors on an interest determining process, since keywords related to a negative feeling are also counted and evaluated by performing the interest determination based on only the occurrence frequency of keywords in the conversation. The negative feeling may include "dislike", "avoid" etc.

It is an object of the present invention to provide an apparatus for providing information for vehicle to more densely collect information reflecting user's hobbies and interests and also respond to various kinds of tastes appropriately.

According to an example of the present invention, an apparatus for providing information for vehicle is provided with the following features. The apparatus includes a conversation inputting means for inputting contents of a conversation of a user in a vehicle, a speech-recognition means for recognizing the contents of the conversation by using a speech recognition, a keyword extracting means for extracting a keyword to be used for an interest determination from the contents of the conversation recognized by the speech recognition, a mental condition detecting means for detecting a mental condition of a user when the contents of the conversation is inputted, a service information collecting means for collecting service information based on the extracted keyword and the detected mental condition, and a service information output means to output the collected service information in a form of an image, audio, or those combination.

According to the above-mentioned configuration, the apparatus detects the mental condition of a user when conversation contents is inputted, then collects the service information based on the keyword extracted from conversation and the detected mental condition. In other words, the apparatus does not use the extracted keyword alone as an interest reflecting information in a uniformly fixed manner. The apparatus performs the interest determination by also considering the metal condition, i.e., the feeling, when the conversation including the keyword is held. Therefore, it is possible to more densely collect information reflecting user's hobbies and interests and also respond to various kinds of tastes which may be momentarily changed according to feeling.

A service information output means can be configured to output the service information in response to acquiring predetermined service trigger information. The service trigger information can be generated in various forms. For example, the apparatus may include a service trigger information input means for inputting the service trigger information of the service information by a user. A service information output means outputs service information when the inputted service trigger information is acquired. According to the configuration, by allowing the user to input the service trigger information in response to the user intent, the user can achieve the service information at any time the user wanted information. The input of the service trigger information can be performed in a manual-operation input or a voice input.

On the other hand, the apparatus may include a service trigger information output means for outputting the service trigger information of the service information when the detected mental condition satisfies a predetermined condition. A service information output means outputs the service information by acquiring the inputted service trigger information. By configuring the apparatus in the above-mentioned manner, it is possible to provide information in a timely manner, since the service information is automatically provided in response to the mental condition of the user in the vehicle without any user input of the service trigger information.

The apparatus may further includes a base data accumulating means for storing and accumulating interest determining base data which includes the keyword, i.e., an extracted keyword, and the detected mental condition information being associated and linked with the keyword. In addition, the apparatus may further include a user interest information extracting means for extracting user interesting information reflecting the user's present interest from the interest determining base data accumulated. An service information collecting means can be configured so that the service information which suits the retrieved user interesting information is collected. According to the configuration, the keywords are stored as the interest determining base data by linking the keyword to the mental condition information at the time of the conversation including the keyword, and the user interesting information reflecting the user's present interest is extracted from the interest determining base data accumulated. Therefore, it is possible to take a user's mental condition into consideration finely for each one of keywords, and to determine a user's interest still more exactly.

In addition, the base data accumulating means may be configured to accumulate only the keyword extracted within a latest predetermined period, and to delete the keyword accumulated for the predetermined period in an orderly fashion. According to the configuration, it is possible to carry out the interest determination by a form of considering the keyword within the latest predetermined period together with the mental condition as important factors. Therefore, it is possible to provide information in a manner that follows adequately to both the user interesting information and the mental condition momentarily changing. The above-mentioned predetermined period where the interest determining base data is accumulated may be defined as a fixed time period to the current time which is measured by a time measuring means. Alternatively, a memory means for the interest determining base data may be configured as the first-in and first-out type having a limited capacity. The memory may be managed to discharge and delete from the oldest one of the interest determining base data in an orderly manner when the memory runs a remaining capacity out due to a progression of data accumulation. In this case, the latest predetermined period is defined as a residual time period in the memory for accumulating the interest determining base data. The residual time period shall be understood to be varied in accordance with the data extracting condition.

The apparatus may further includes a mental condition quality determining means for determining a quality, i.e., good or bad, of the detected mental condition. In this case, the base data accumulating means handles the result of the mental condition quality determining means as the mental condition information that is associated and linked with the keyword, and accumulates a pair of the result of the mental condition quality determining means and the linked keyword as the interest determining base data. In this case, the service information collecting means may be a means for searching service information to be collected by using the keyword extracted by the keyword extracting means. A user who talks about a keyword having a high interest for an interesting object usually feels a pleasant feeling. This feeling usually makes the mental condition of the user at talking to shift to a side corresponding to a good feeling side. On the contrary, in the case that the user talks about a keyword related to an object that is less attractive or is expected to avoid positively, the mental condition of the user at talking shifts to a side corresponding to a poor feeling side. Then, the above-mentioned user interest information extracting means is configured to give a higher ranking of an adopting priority for searching of the service information in the service information collecting means to a keyword which has a better result of the mental condition quality determination in the interest determining base data. According to the above configuration, a keyword which has a poor result of the mental condition quality determination is set at a lower ranking of the adopting priority for searching the service information in the service information collecting means. Therefore, the keyword having a poor result of the mental condition quality determination, i.e., the keyword spoken at a poor mental condition, is withdrawn from the searching for the service information. If the keyword having a poor result of the mental condition quality determination is not withdrawn, it is at least handled to perform a limited contribution to the searching.

The user interest information extracting means may be configured as a means for analyzing the frequency of occurrence of the keyword accumulated in the base data accumulating means, and for giving and setting a higher ranking of the adopting priority for searching the service information to the keyword which has a higher occurrence frequency and better result of the mental condition quality determination. By using a keyword having a higher occurrence frequency in the conversation, it is possible to determine a present interest of the user more exactly.

The user interest information extracting means may include a keyword dictionary storage section which storages a keyword dictionary which covers a group of keywords selected and prepared beforehand for a purpose of determining an interest. The keyword extracting means may be configured as a means for selectively extracting a keyword stored in the keyword dictionary by decompositing the content inputted via the speech recognition into words, and comparing and looking up the decomposition result with the key word dictionary. In the conversation held by a user, a group of the keywords useful as a key of a user's interest estimation is restricted comparatively. Therefore, by arranging and installed the keyword dictionary in the apparatus, and selectively extracting a keyword stored in the keyword dictionary, it is possible to determine a user's interest more exactly. In this case, the user interest information extracting means may be configured to include a keyword update information acquiring means for periodically acquiring keyword update information which contained a new group of keywords related to a season, fashion, or the newest topic via an external network, and a keyword dictionary renewing means for renewing or updating the keyword dictionary based on the acquired update information. In this way, the contents of the keyword dictionary can be rearranged in an optimal fashion according to a change of a season, fashion, or the newest topic, and, as a result, a timely interest determination can be performed.

On the other hand, the user interest information extracting means may also be configured so that a keyword which is linked with the mental condition quality determination result poorer than a predetermined level in the interest determining base data is not adopted for searching the service information in the service information collecting means. It is possible to improve an accuracy of interest determination based on the keyword, by not adopting the keyword spoken in the condition where the mental condition is below a predetermined level for searching purpose.

The mental condition quality determining means may be configured to include mental point converting means for converting a mental condition detected by the mental condition detecting means into a mental point which is defined to have a larger numerical value as the mental condition becomes better. The base data accumulating means may be configured to accumulate the interest determining base data which is provided by handling the mental point as the mental condition information to be associated and linked with the keyword. By converting the mental condition of each extracted keyword into a numerical form such as the mental point, and putting a weighing indicative of a contribution amount of a keyword by linking each keyword for determining interest with the mental point, it is possible to determine the mental condition by taking the mental condition into consideration more exactly. For example, the user interest information extracting means may be configured to sum the mental point for each classification of the keywords accumulated in the base data accumulating means, and to give a higher ranking of the adoption priority for searching the service information in the service information collecting means to the keyword as the totaled point of the mental point for the keyword becomes higher. According to the above configuration, the keyword spoken at a good mental condition may have a higher totaled point than that of the keyword spoken at a poor mental condition. Therefore, the apparatus treats the keyword having the higher sum points as a predominance one in the searching for the service information even if the occurrence frequency of the keyword itself is somewhat low. As a result, it is possible to improve accuracy for determining an interest based on the keyword.

On the other hand, the mental point converting means may be configured to set a value of zero or negative to the mental point associated and linked with a keyword that is contained in a conversation when the mental condition is poorer than a predetermined level. According to the above configuration, when the mental condition is poorer than the predetermined level, the mental point is set to zero for example. Therefore, despite the keyword actually appears in the conversation, the apparatus handles and treats the keyword as same as a keyword that does not appear in the conversation. As a result, it is possible to reasonably withdraw a keyword reflecting a negative interest object from the searching. In addition, in a configuration that is able to set a negative value to the mental point, it is possible to provide the following advantage. This advantage may be achieved in a case where the same user speaks the same keyword many times in a series of conversation, or a plurality of users speak the same keyword in a series of conversation. In the above case, the same keyword may be spoken at both the good mental condition and the poor mental condition in a mixed fashion. Even in this situation, according to the configuration, the apparatus does not simply count an occurrence of the keyword. The apparatus may cancel the contribution of the mental point of the keyword spoken at the good mental condition and the contribution of the mental point of the keyword spoken at the poor mental condition. As a result, it is possible to determine interest still more exactly. In this case, the user interest information extracting means may be configured to withdraw a keyword having zero or negative total value of the mental points from the searching of the service information in the service information collecting means.

The service trigger information output means may be configured to output the service trigger information for the service information when total of the mental point for the extracted keyword exceeds a predetermined threshold value. The service information output means may be configured to output the service information by acquiring the service trigger information inputted. In this case, it is different from a case where the service trigger information is outputted by a user input, the service trigger information is outputted automatically when total of the mental point exceeds the predetermined threshold value. As a result, since the service information can be provided in a timely manner when mental conditions of participants in a conversation are uplifted all at once by an interest object reflected on the specific keyword, it is possible to further uplift an atmosphere in the vehicle.

The mental condition detecting means may be configured to include an echo measuring unit which performs an echo measurement on the heart or the lung of the user who is sitting on the seat of the vehicle, and to detect a mental condition based on the echo measurement result. The heart and the lung have a remarkable motion as beating and breathing, therefore, by supplying an ultrasonic wave as a detection probe, the heart and the lung produce a reflected wave with the Doppler effect indicative of the motion. The heart and lung are usually change an action clearly and promptly in response to a mental condition. Therefore, a mental condition can be detected in a real time manner with sufficient accuracy by analyzing the above-mentioned reflected wave. The echo measuring unit may be configured to perform an echo measurement on a user. For such purpose, the echo measuring unit may have an ultrasonic supplying section and an ultrasonic receiving section both embedded in a seat back portion of a seat. The echo measurement can be carried out with high precision by establishing the ultrasonic transmission part for measurement, and a reflection ultrasonic wave receive section in the location which attends a user's back in a direct this slack backrest part at the heart or a lung.

Since at least one of a heart rate, a breathing rate, and blood flow velocity of a user can be obtained by echo measurement of the heart or the lung, the mental condition detecting means can detect a mental condition of the user based on the result obtained. In the heart echo waveform, a frequency Doppler shift arises according to a cardiac beat. The Doppler shift becomes the minimum, since a drift speed of a cardiac muscle becomes the minimum when a variation rate of an expansion or contraction direction of a cardiac muscle becomes the maximum. The Doppler shift becomes the maximum, when a cardiac muscle passes through a neutral position. Therefore, by converting a heart echo waveform into a frequency-time base waveform, it is possible to detect, for example, a heart rate from a period of cycle of the waveform, and a strength of heart beat from an amplitude of the waveform. Similarly, by converting a lung echo waveform into a frequency-time base waveform, it is possible to detect a breathing rate from a period of cycle of the waveform, and a depth of the breathing from an amplitude of the waveforms. In addition, a blood flow flowing in the heart may also be a factor of the Doppler shift on the heart echo waveform. Therefore, by adjusting a wavelength of an ultrasonic beam supplied, it is possible to calculate a blood flow velocity from the heart echo waveform.

The mental condition detecting means may be configured to have a first echo measuring section, a second echo measuring section, and a differential calculation section. The first echo measuring section includes an ultrasonic transmission part and a reflection ultrasonic receiving part both made for a first measuring target such as a heart and/or a lung. The second echo measuring section includes an ultrasonic transmission part and a reflection ultrasonic receiving part both made for a second measuring target that includes human body portions other than the first measuring target. The differential calculation section calculates and outputs a differential waveform between an output waveform from the reflection ultrasonic receiving part of the first echo measuring section and an output waveform from the reflection ultrasonic receiving part of the second echo measuring section. The mental condition detecting means may be configured to determine at least one of a heat rate, a breathing rate, and a blood flow velocity based on the differential waveform. It is possible to observe a Doppler shift reflecting movement of the heart or the lung by monitoring a reflected waveform of an ultrasonic wave that is supplied from the outside of a human body and reached to the heart and/or the lung. However, besides the movement of the heart and the lungs, a user's posture change, a vehicle vibration acting on a user human body, a blood flow in the human body organization of those other than the above-mentioned internal organs, etc., may be a factor for a Doppler shift and may be turned into causes of error. To address the above problem, the apparatus subtracts the output waveform from the reflection ultrasonic receiving part of the second echo measuring section targeted the human body portions other than the first measuring target from the output waveform from the reflection ultrasonic receiving part of the first echo measuring section targeted the heart and/or the lung. The human body portions other than the first measuring target are human body portions located apart from the heart and the lung. By this measure, it is possible to effectively eliminate the Doppler shift factors other than the movement of the heart and/or the lung.

In addition, it is easy to determine a degree of mental activity based on the heart rate and/or the breathing rate indicated by an echo measurement result. However, in a case of identical degree of the mental activities, it is difficult to judge correctly whether the mental activity is leaning to a pleasant side, i.e., in a good mood, or an unpleasantness side, i.e., in a bad mood. To address the above problem, the mental condition detecting means may further include a pleasant degree detecting means, disposed separately from the echo measuring unit, for determining the pleasant degree of the mental condition. The mental condition detecting means may be configured to determine the degree of the mental activity based on the result of the measurement of the echo measuring unit, and to determine the mental condition based on a combination of the degree of the mental activity and the pleasant degree of the mental condition. The pleasant degree detecting means may be a means for detecting the pleasant degree based on, for example, at least one of a expression, a sight direction, and a posture of the user.

Usually, a user in a vehicle pay attention in a concentrated manner into a point that relates to a present user interest such as where to go from now, or where to visit during the trip even when the destination has been decided. To meet such a user interest, the service information outputting means may be configured to include a car-navigation system. The information collecting means may be configured so as to search and collect destination information which suits user interesting information as service information on the car-navigation system. As a result, it is possible to navigate the user to the destination which suits the determined interest exactly.

On the other hand, in a case that the service information outputting means includes a wireless access device to websites on the Internet, the service information collecting means may be configured so as to search and collect the website information on the Internet as the service information which suits the user interesting information. Thereby, in response to the determined interest, it is possible to satisfy the user by allowing a timely access to the Internet website that suits the determined interest. In addition to or instead of the above described examples, it is possible to play a video data, an image data or a music data by reading out from a library in an in-vehicle service information storage section, or by downloading from an external network via a wireless connection.

In addition, service information could become useless or obsolete due to repeated outputs and serves of the same service information during repeated use of the vehicle by the same user. In this case, the service information output means may include an output-history-information record means for recording output history information of the service information outputted by the service information output means. In this case, the service information collecting means may be configured to give priority for collecting relatively new service information that can be identified as one that has less number of output record in the output history information than a predetermined threshold number for a last predetermined period. Thereby, it is possible to serve fresh service information even for the same user. There may be a case where a search result is not desirable when the service information collecting means performs a first search using the extracted user interesting information. For example, there may be a case where a search hit number about the service information that has less number of output history than a predetermined threshold times for the latest predetermined period in the output history information. In this case, it is possible to broaden candidates of service information by carrying out a second search that has broadened narrowing-down conditions than the first search.

Then, the service information collecting means may be able to select a keyword which the user has a good feeling based on the mental condition detected by the mental condition detecting means, and to collect service information only based on the selected keyword.

BRIEF DESCRIPTION OF THE DRAWINGS

Additional objects and advantages of the present invention will be more readily apparent from the following detailed description of preferred embodiments when taken together with the accompanying drawings. In which:

FIG. 13 is an explanatory diagram showing an example of extracted keywords and obtained mental points for a first conversation example;

FIG. 14 is an explanatory diagram showing storage states of the keyword memory corresponding to a case shown in FIG. 13;

FIG. 15 is an explanatory diagram showing mental point statistical data for each keyword corresponding to a case shown in FIG. 14;

FIG. 16 is a schematic diagram showing an example of output of the search results in a case of performing narrowing process;

FIG. 17 is a plan view of a display showing a first display example of a destination setting screen in response to a search results of FIG. 16;

FIG. 24 is an explanatory diagram showing an example of extracted keywords and obtained mental points for a second conversation example;

FIG. 25 is an explanatory diagram showing storage states of the keyword memory corresponding to FIG. 24;

FIG. 26 is an explanatory diagram showing mental point statistical data for each keyword corresponding to a case shown in FIG. 25;

FIG. 28 is an explanatory diagram showing an example of extracted keywords and obtained mental points for a third conversation example;

FIG. 29 is an explanatory diagram showing mental point statistical data for each keyword corresponding to a case shown in FIG. 28;

DETAILED DESCRIPTION OF THE PREFERRED EMBODIMENTS

Figure 1:
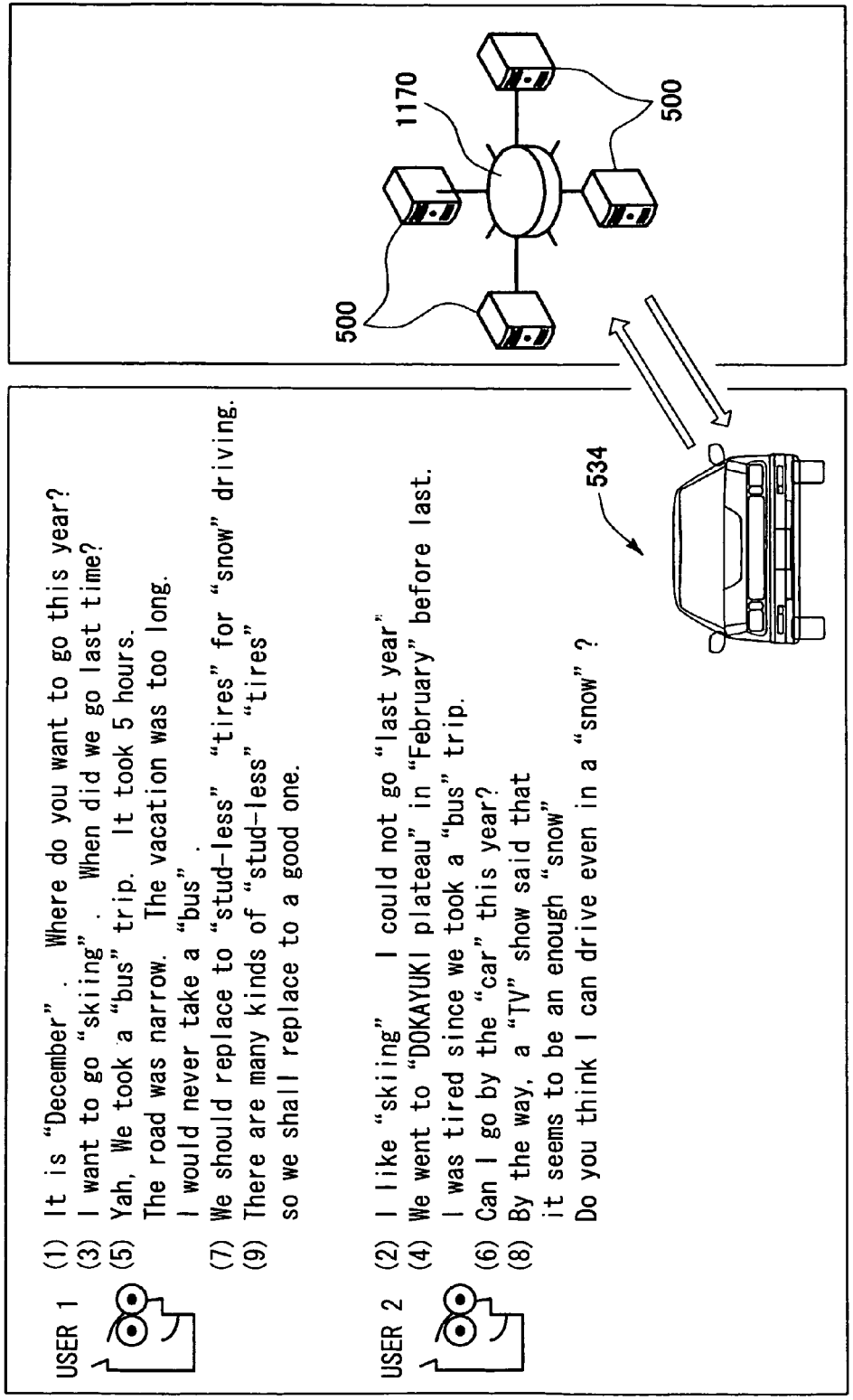
FIG. 1 is a schematic view of the apparatus for providing information for vehicles of the present invention.
Figure 2:
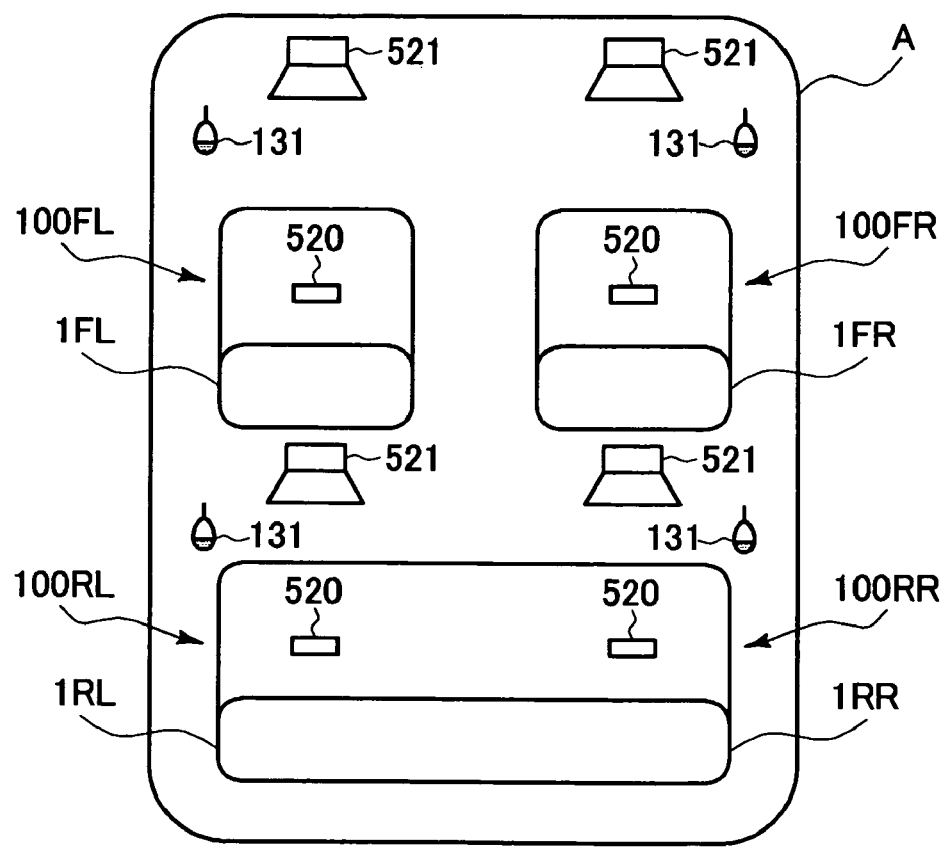
FIG. 2 is a plan view of a vehicle showing an arrangement of microphones for a speech recognition.

Hereinafter, an embodiment of the present invention is described in detail while using attached drawings. FIG. 1 is a schematic view of the apparatus for providing information for vehicle, i.e., a vehicle information providing apparatus, of the present invention. The vehicle information providing apparatus 534 is mounted on a vehicle, i.e., a car, in a fixed fashion. As shown in FIG. 2, the seating sensors 520 are arranged on each seat of the vehicle A. The seat includes a driver seat 1FR, a passenger seat 1FL, and backseats 1RR and 1RL. In addition, face cameras 521 which captures a face image of a user, i.e., a person on the vehicle, seating on each seat is provided respectively. Further, a microphone 131 which inputs conversation in the vehicle held by the users seating on each seat in an audio form is provided. The microphone provides means for inputting a conversation.

Before use of the vehicle, the user on each seat is identified by identification. In this embodiment, the identification is carried out by matching the face image. For this purpose, the face cameras 521 are designed and arranged to take frontal images on each seat 100 FR, FL, RR, and RL to cover each passenger's upper half of the body. The seating sensors 520 are provided by load sensors etc. which are embedded in a seat portion of the each seat 100 FR, FL, RR, and RL, and detect the passenger seated thereon in an auxiliary manner. For example, the apparatus may detects a seating on a certain seat if both a detection of load on the seat by the seating sensor 520 and a detection of the face image of the certain potential user in an imaging range of the face camera 521a are met. By using this measure, it is possible to avoid erroneous detection caused by a luggage loaded on the seat or a disturbance light etc. In addition, an auxiliary use of the seating sensor 520 allows the apparatus to perform a certain accuracy for seating detection even if an accuracy of the face image matching is lowered, and enables the apparatus to use a lighter algorithm. The vehicle information providing apparatus 534 includes a memory, e.g., a flash memory 109 in FIG. 3, to provide a user registration part. The user registration part stores and memorizes face feature amount extracted from each user's master face image in a manner that the face feature amount is associated and linked with a user ID. The apparatus is configured to determine which user is seating on which seat by matching the face feature amount in the memory with a face feature amount extracted from the face image captured by the face camera 521 for each seat.

Figure 3:
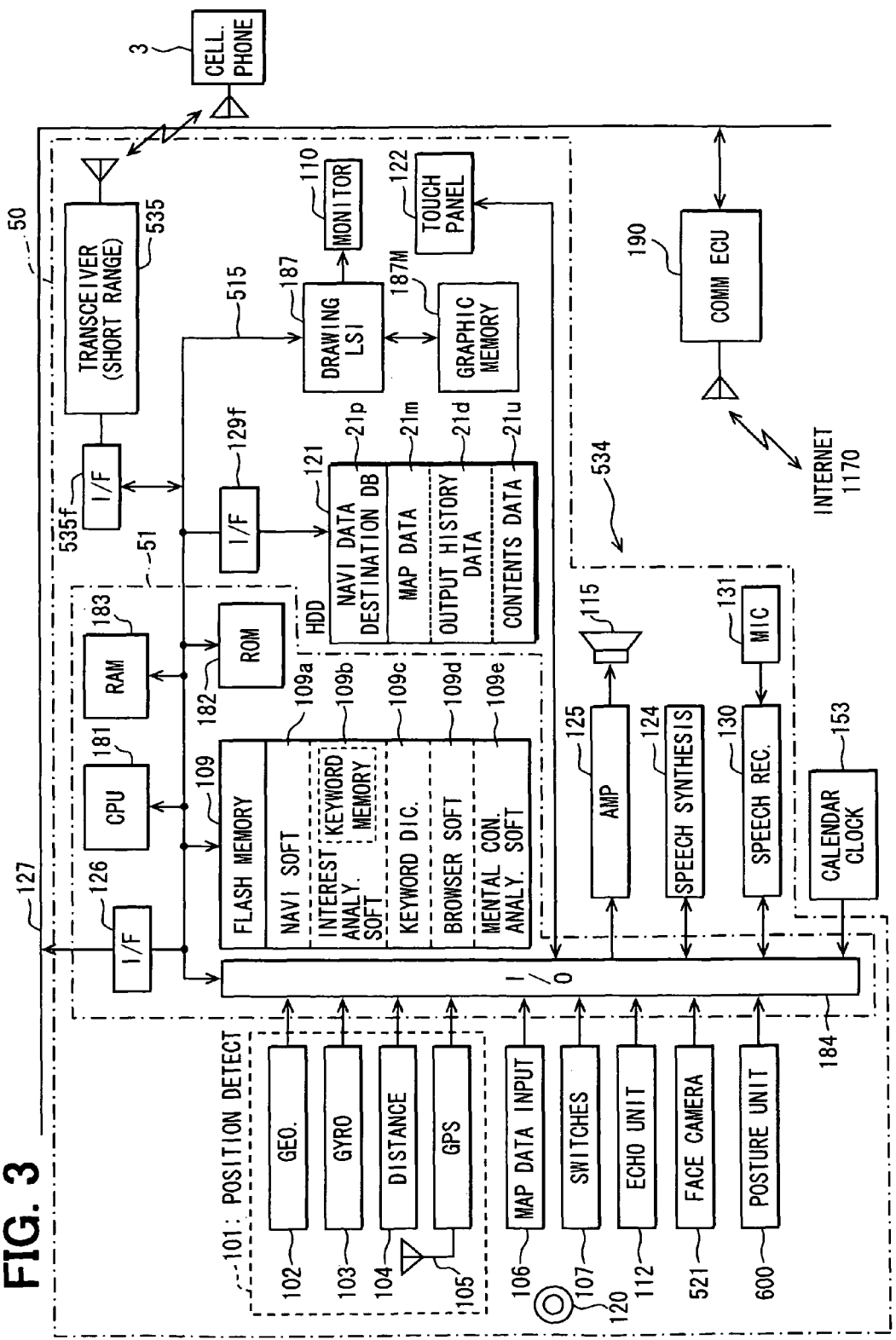
FIG. 3 is a block diagram showing an electronic configuration of the vehicle information providing apparatus.

Next, FIG. 3 is a block diagram showing an example of configuration of the vehicle information providing apparatus 534. The vehicle information providing apparatus 534 is provided as a car navigation apparatus in this embodiment. In detail, the apparatus includes a position detecting device 101, a map data input device 106, a group of operation switches 107, and a remote control sensor 111 that may be referred to as a remote control device. The apparatus further includes a speech synthesis device 124 for voice guidance, a speaker 115 for outputting synthesized voice, and a flash memory 109 that is nonvolatile memory. The apparatus further includes a monitor 110 made of LCD etc., an information system ECU 51 that is connected with the components and functions as a main control section, and a HDD 121, i.e., a hard disk drive, that provides a main storage.

The position detecting device 101 has a well-known magnetic field sensor 102, a gyroscope 103, a distance sensor 104, and a GPS receiver 105 for GPS which detects the location of the vehicle based on the radio wave from satellites. Since each sensors has an error from which character differs, the sensors 102, 103, 104, and 105 are arranged and used to complement each other. Alternatively, depending on a required accuracy, the system may include only a part of the above mentioned sensors, and may includes additional sensors such as a rotation sensor of the steering, the wheel rotation sensors of rotatable wheels, etc.

For the group of the operation switches 107, it is possible to use mechanical switches etc., but in the embodiment, the system also includes a touch panel 122, which is unitary formed with the monitor 110, for providing a software buttons. The touch panel 122 enables it to recognize an operation condition which is obtained by touching the touch panel area corresponding to a button image displayed on the monitor 110. It is possible to input various command by these operation switches 107.

It is also possible to use the speech recognition unit 136 for inputting various command, in addition to the operation switches 107. This inputs a voice from the microphone 131 shown in FIG. 2 and connected to the speech recognition unit 130, carries out speech-recognition processing by the speech recognition technology available, and changes the input voice into operating command according to the recognition result.

The information system ECU 51 is mainly made of a micro computer hardware in which a CPU 181, a ROM 182, a RAM 183, the above-mentioned flash memory 109, and the input and output part 184 are connected via a bus 515. The HDD 121 is connected to the bus via an interface 129f. Similarly, a drawing LSI 187, which carries out image outputting to the monitor 110 based on drawing information for displaying a map and a navigation operation screen, and a graphic memory 187M for drawing processing are connected to the bus. Further, the above-mentioned monitor 110 is connected to the above. The CPU 181 performs control for a destination search and/or a route guidance with a navigation software 109a and data which were memorized by the flash memory 109. The navigation software performs as a service information collecting means. A control of reading and writing of data of the HDD 121 is performed by the CPU 181.

The map data 21m containing road data and navigation data 21p which includes data of destinations and guide information of destinations are stored in the HDD 121. The HDD 121 also stores output history data 21d and contents data 21u. It is possible to rewrite the contents of those data by instructing the apparatus via operation of the operation switches 107, operation of the remote control terminal 112 or voice commanding of an audio input. It is also possible to update the contents of the HDD 121 based on data read from the storage medium 120 using the external information input-output device, i.e., the map data input device 106. In this embodiment, the information system ECU 51 is connected to the serial communication bus 127 providing a network in the vehicle via a communication interface 126, and exchanges data among other control devices in the vehicle, such as a vehicular body system ECU and an engine control ECU, not illustrated.

A communication ECU 190, i.e., a wireless access means, including a wireless transmission and reception part for the internet connection 1170 is connected to the serial communication bus 127. The browser software 109d is installed in the flash memory 109. Therefore, the system can access a contents providing server 500, i.e., an information service server, shown in FIG. 29, which obtains websites, via the communication ECU 190 by specifying the URL, and can retrieve files of the contents. Contents of the file, i.e., contents of the homepage, is served via the monitor 110 in case of image including an animation and a still image, and via the speaker 115 through the amplifier 125 in case of sound. Those devices may be referred to as a service information outputting means. The flash memory 109 stores interest analysis software 109b, a key word dictionary 109c, browser software 109d, and mental condition analysis software 109e. The interest analysis software 109b provides a keyword extracting means and a user interest information extracting means. The browser software 109d provides a service information collecting means. The mental condition analysis software 109e provides a mental condition quality determining means and a mental point converting means. The detail of above feature is described later.

The monitor 110, i.e., one of the service information output means, is made of a color liquid crystal display. The monitor 110 displays a present position mark of the vehicles inputted from the position detecting device 101, a map data 21m inputted from HDD 121, and additional data, such as a guidance route on the map in a overlapping manner. Further, as mentioned above, the touch panel 122 is overlapped thereon, therefore, the monitor 110 also displays function buttons for destination setting, display setting, various function calls, screen changing operations, etc. when need arises.

The vehicle information providing apparatus 534 functions by initiating the navigation program 21p by the CPU 181 of the information system ECU 51. Then, a driver chooses a desired destination from the destination data base 21d by operating the operation switches 107 or commanding in audio from the microphone 131. For example, the following processing are carried out, when route guidance processing for displaying a route to the destination on the monitor 110 is chosen from the menu displayed on the monitor 110. That is, the system inputs a destination based on a driver's operation via the map or a destination choice screen on the monitor 110, and performs processing for searching an optimal route to the destination from the current position which is acquired based on the satellite data obtained from the GPS receiver 105. Then, the system provides guidance of the optimal route to the driver by displaying a guidance route on the road map on the monitor 110 in an overlapping manner. A Dijkstra method etc., are known as a method for setting an optimal route automatically. The system further performs a reporting of message indicating an operational condition, and/or providing a guidance for operation by using at least one of the monitor 110 and the speaker 115.

Figure 5:
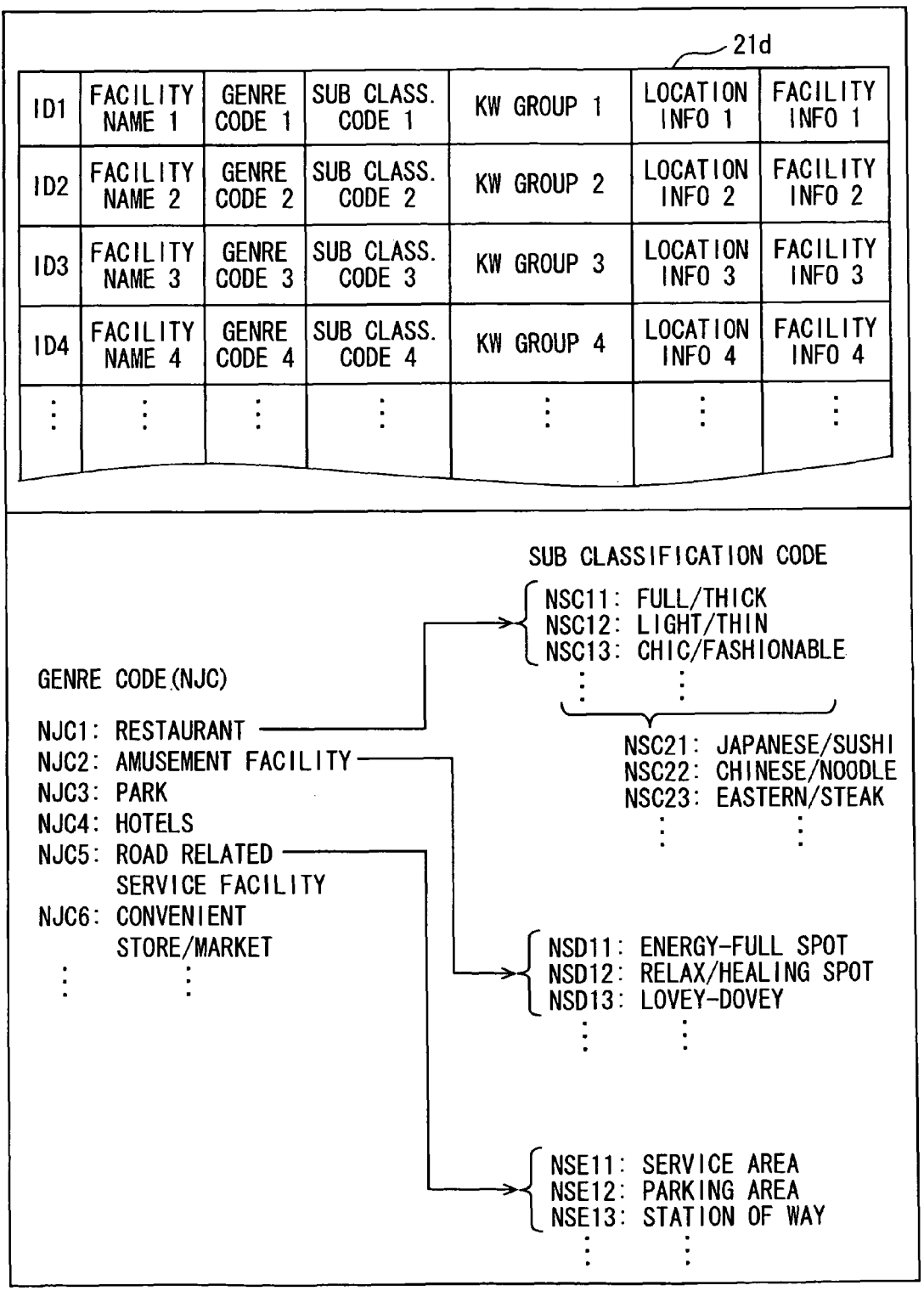
FIG. 5 is a schematic diagram showing an example of navigation data.

FIG. 5 shows configuration of contents of the destination data base 21d in which each of the location information of destinations is associated with and linked to an ID for pinpointing each destination, a classification information and keywords. The keywords are selected from a keyword group registered in the key word dictionary 109c shown in FIG. 3, which is a keyword group for determining a user interest, so that the keywords have a close relationship with the destination.

On the other hand, the classification information includes a genre code and a sub classification code. The genre code classifies the institution, which is selectable as the destination, according to the purpose classification, such as a restaurant, an amusement facility, a park, a hotel, a road related service facility, a convenience store, a supermarket, etc. Among these, the restaurant, the road related service facility, a convenience store, a supermarket, etc. are categorized as a food providing facility where it is possible to have a drink and food.

Each genre code is further categorized by attached sub classification code which suites the genre code. For example, in the case of the restaurant, the classification of the sub classification code is determined so that it is enabled to select the destination in accordance with the user's physical and/or mental condition by taking an effect of the hospitality into consideration. For example, the restaurant, which should be chosen when the user feels a good physical condition, feels a good appetite, or is in a high hunger degree, is classified with a sub classification code corresponding to a priority for fullness, such as a full and thick food. This kind of restaurant may be suit for youth or manhood. The restaurant, which should be chosen when the user does not feel a good physical condition, does not have a good appetite, or is not so hungry, is classified with a sub classification code corresponding to a priority for lightness, such as a light and thin food. This kind of restaurant may be suite for woman. For example, the restaurant, which should be chosen when the user is depressed and wants to change feeling, or wants to increase a lovely feeling with other person, is classified with a sub classification code indicating a priority for comfortable atmosphere, such as a chic and fashionable food. Further, another sub classification code, which indicates a general food or cooking kinds, such as "Japanese style and Sushi", "Chinese and Noodle", and "European and Curry", is also provided separately and may be selected.

For example, in the case of the service provision institution for a recreation or entertainment purpose, such as an amusement facility or a sightseeing spot, the classification of the sub classification code is determined so that it is enabled to select the destination in accordance with the user's physical and/or mental condition. For example, the facility, which should be chosen when the user feels a good physical condition, or wants to have a cheerful and active service, is classified with a sub classification code corresponding to a priority for physical or mental relief, such as a energy full spot. This kind of facility may be suit for youth or manhood. The facility, which should be chosen when the user does not feel a good physical condition or even feels tired, is classified with a sub classification code corresponding to a priority for suppressing exhaustion, such as a relaxing and healing. This kind of facility may be suite for woman. The sub classification code focused on comfortable atmosphere, such as a lovely spot, is given to the facility or institution which should be chosen to heap up a mood in a couple etc.

On the other hand, the road relating service institution is further categorized with a sub classification code indicating a service area on a highway, a parking area on a highway, a station of a way, and a drive-in area.

Figure 20:
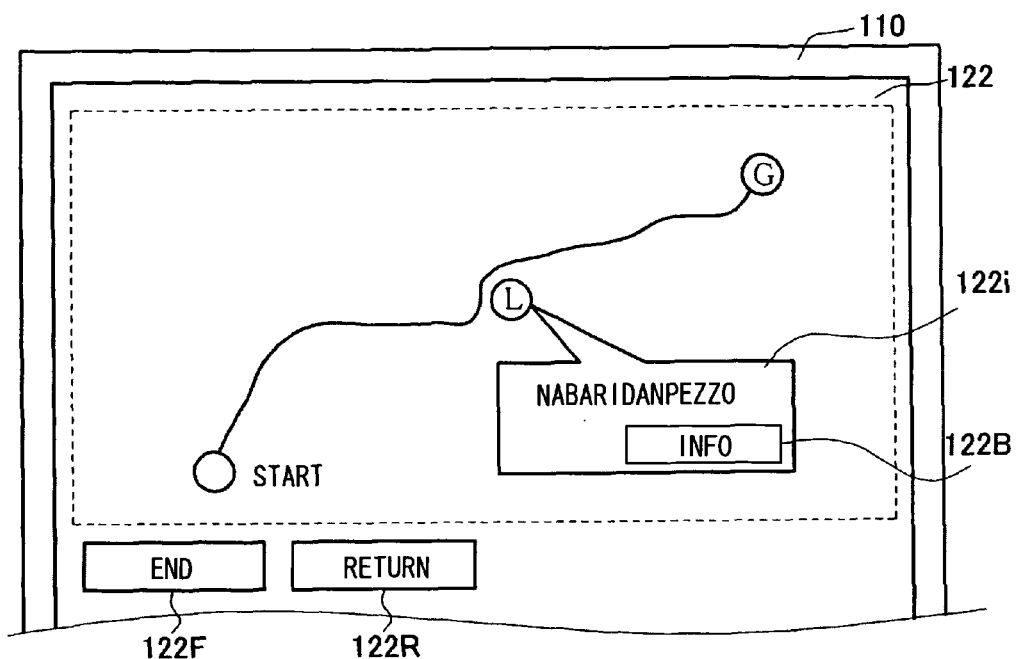
FIG. 20 is a plan view of a display showing a second display example of a destination setting screen in response to the search results of FIG. 16.

In destination data base 21*d*, a content explanation information of each facility or destination, i.e., a contents information of the facility, is also stored in an associated and linked manner. The system displays contents explanation information corresponding to the selected destination on the screen as shown in FIG. 20 or outputs it in a voice form, so that the user may confirm the contents before arriving at the destination and use it as one of selection aid.

Figures 6, 7:
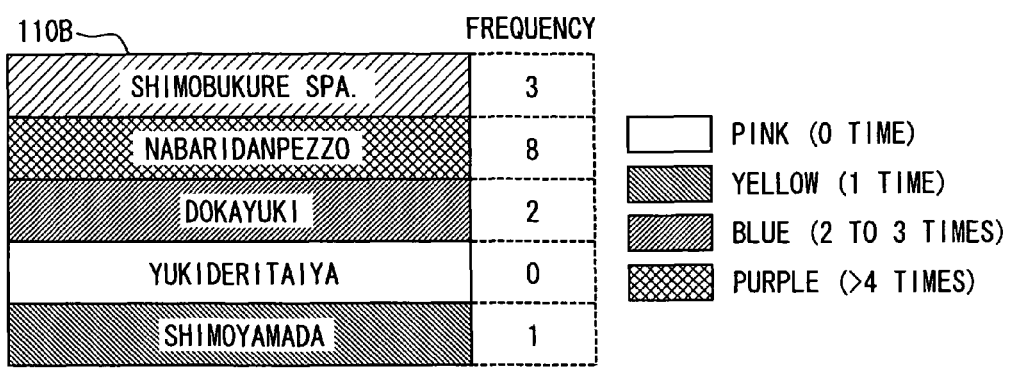
FIG. 6 is a schematic diagram showing an example of output history data.
FIG. 7 is a schematic diagram showing a first example of output of a search result.

Next, an output history data 21*d* in the HDD 121 records and stores visited destination histories, i.e., destination history, within a past predetermined period, e.g., one to five years, or to a predetermined numbers, e.g., 30 to 300 destinations, in an associated and linked manner with a visiting day, a user name, a classification, and visiting frequency, as shown in FIG. 6. Update of the output history data 21*d* may be performed at a timing when a route guidance to the destination by the car-navigation system is completed. At the update timing, the visited destination history may be newly stored in the output history data 21*d*, or the visiting frequency for the existing destination may be incremented. A user identification may be performed by the well-known face authentication technology using a captured image after capturing a face of user on each seat by the camera provided for each seat.

Contents files, which were already downloaded and viewed, from websites that are related to the visited destinations, are stored in a contents data 21*u* in the HDD 121, and are prepared for reviewing at any time. Although it is not illustrated, image data, music data, etc. different from the contents files of the websites are associated with and linked to the group of keywords and a destination name reflecting the user interest, and are also prepared in the contents data 21 as service information.

The echo measuring unit 112 is connected to the input and output part 184. The echo measuring unit 112 is a principal part of a mental condition detecting means, and performs echo measurement of the heart H of the user who sits down on the seat of the vehicle. An echo measuring waveform, i.e., a result of a measurement, is analyzed by the CPU 181 by executing the mental condition analysis software stored in the flash memory 109. The system detects and determines a mental condition based on the output from the above analysis. The heart has a remarkable motion as a beat of the heart. Therefore, by supplying an ultrasonic wave as a detection probe, the heart produces a reflected wave with the Doppler effect indicative of the motion. The heart usually changes an action clearly and promptly in response to a mental condition. Therefore, a mental condition can be detected in a real time manner with sufficient accuracy by analyzing the above-mentioned reflected wave.

The echo measuring unit 112 has the ultrasonic transmission part 1070 and 1080 and the reflection ultrasonic receiving part 1090 and 1100 which are embedded in a backrest part 150 of the seat. The ultrasonic transmission part comprises well-known ultrasonic transducers. In addition, although the reflection ultrasonic receiving part may include a common microphone, if consistency of an acoustic feature is taken into consideration, it is desirable to include an ultrasonic transducer of the same kind as used in the ultrasonic transmission part.

In detail, the mental condition detecting means may be configured to have a first echo measuring section, a second echo measuring section, and a differential calculation section. The first echo measuring section includes an ultrasonic transmission part 1070 made and arranged for measuring the heart H, i.e., a measuring target, and a reflection ultrasonic receiving part 1090. The second echo measuring section includes an ultrasonic transmission part 1080 made and arranged for measuring human body portions not including the heart H and the lung, and a reflection ultrasonic receiving part 1100. The target area of the second echo measuring section is around the backbone below a diaphragm in this embodiment. The differential calculation section 1040, 1050, and 1060 calculates and outputs a differential waveform between an output waveform from the reflection ultrasonic receiving part 1090 of the first echo measuring section and an output waveform from the reflection ultrasonic receiving part 1100 of the second echo measuring section.

It is possible to observe a Doppler shift reflecting movement of the heart or the lung by monitoring a reflected waveform of an ultrasonic wave that is supplied from the outside of a human body and reached to the heart and/or the lung. However, besides the movement of the heart and the lungs, a user's posture change, a vehicle vibration acting on a user human body, a blood flow in the human body organization of those other than the above-mentioned internal organs, etc., may be a factor for a Doppler shift and may be turned into causes of error. To address the above problem, the apparatus subtracts the output waveform from the reflection ultrasonic receiving part 1100 of the second echo measuring section targeted the human body portions not including the heart H or the lung from the output waveform from the reflection ultrasonic receiving part 1090 of the first echo measuring section targeted the heart H or the lung. By this measure, it is possible to effectively eliminate the Doppler shift factors other than the movement of the heart H or the lung. In detail, in the differential calculation section, one of the output wave of the reflection ultrasonic receiving part 1090 of the first echo measuring section and the output wave of the reflection ultrasonic receiving part 1100 of the second echo measuring section is inverted by an inverted amplifier 1040. In addition, a phase adjustment is carried out on one of the output waves by a phase shifting device 1050. In this embodiment, the output of the reflection ultrasonic receiving part 1090 of the first echo measuring section is inputted into the inverted amplifier 1040. The output of the reflection ultrasonic receiving part 1100 of the second echo measuring section is inputted into the phase shifting device 1050. Then, those outputs are compounded with an adder 1060. Alternatively, it is possible to eliminate the inverted amplifier 1040 by replacing the adder 1060 with a differential amplifier. For example, the phase shifting amount of the phase shifting device 1050 is controlled in a feedback manner so that the integrated amplitude of the output wave of an adder 1060 is minimized.

Figure 4:
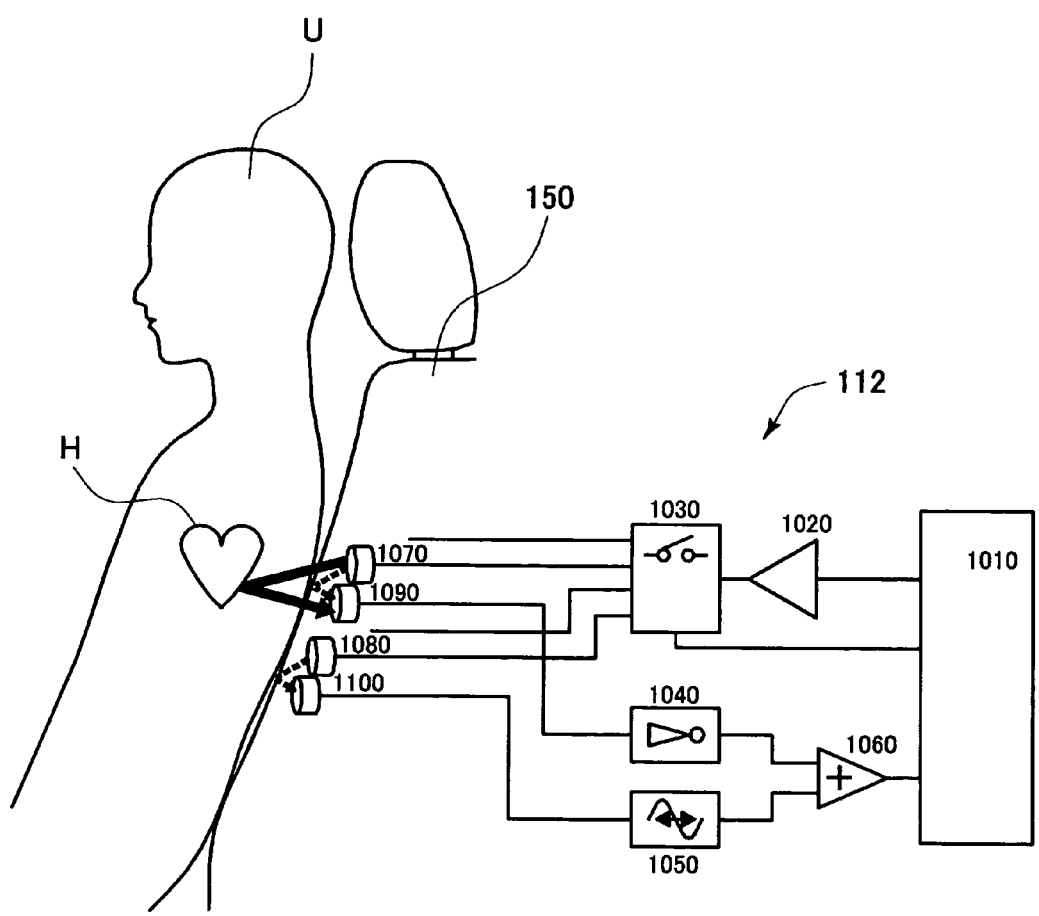
FIG. 4 is a block diagram showing a configuration of an echo measuring unit.

Although only one pair of the ultrasonic transmission part 1070 and the reflection ultrasonic receiving part 1090 for the first echo measuring section is illustrated in a location where the heart can be targeted, in FIG. 4, for example, the other one of the first echo measuring section may be disposed on a location where the lung can be targeted. The first echo measuring section which targets the lung would be one that detects a lung motion for breathing. In addition, since the locations of the heart and the lung differ for every user, in order to optimize the echo measuring point for detecting a motion of the heart and the lung, it is possible to dispose the first echo measuring sections in a plurality of locations corresponding to the heart and/or the lung in a dispersed fashion. The plurality of the first echo measuring sections share an amplifier 102 used as the driving source of the ultrasonic transmission part. The plurality of the first echo measuring sections are suitably selected by a switch 1030 according to a command from the control unit 1010 and used.

Since at least one of the heart rate, the breathing rate, and the blood flow velocity of the user can be obtained by echo measurement of the heart or the lung, the mental condition analysis software 109e executed by the CPU 181 determines a mental condition of the user based on the result obtained. For example, in case of the cardiac beat, the frequency Doppler shift originated in the cardiac beat appears on the heart echo waveform which is the reflection ultrasonic waveforms. The Doppler shift becomes the minimum, since a drift speed of a cardiac muscle becomes the minimum when a variation rate of an expansion or contraction direction of a cardiac muscle becomes the maximum. The Doppler shift becomes the maximum, when a cardiac muscle passes through a neutral position. Therefore, by converting a heart echo waveform into a frequency-time base waveform, it is possible to detect, for example, a heart rate from a period of cycle of the waveform, and a strength of heart beat from an amplitude of the waveform. Similarly, by converting a lung echo waveform into a frequency-time base waveform, it is possible to detect and calculate a breathing rate from a period of cycle of the waveform, and a depth of the breathing from an amplitude of the waveforms. In a configuration illustrated in FIG. 4, a waveform processing part is mainly configured by a DSP etc. in the control unit 1010. The waveform processing part converts the input waveform from the adder 1060 into a frequency-time base waveform, and calculates the heart rate and the strength of beat and/or the breathing rate and the depth of breathing based on a peak analysis of the frequency-time base waveform. Then, the waveform processing part transmits a result of calculation to the CPU 181.

A blood flow flowing inside the heart is one of the Doppler shift factor on the heart echo waveform. By adjusting the wave length of the ultrasonic beam to be supplied, it is also possible to compute the blood flow velocity from the heart echo waveform. For example, in case of detecting a cardiac beat, the wave length of the ultrasonic beam may be adjusted so that a reflection is maximized at an acoustic impedance difference between an outside surface of the heart and the human body organization adjacent to the outside surface of the heart. For example, in case of detecting a blood flow velocity, the wave length of the ultrasonic beam may be adjusted so that a reflection is maximized at an acoustic impedance difference between a ventricle wall surface and the blood which touches the ventricle wall surface.

In this embodiment, the mental condition analysis software determines and classifies each personal mental condition based on the concept of so-called Russell-Mehrabian's feeling plane where the degree J of mental activity, i.e., degree of arousal, is projected on the vertical axis, and the degree I of pleasure is projected on the horizontal axis. In detail, the feeling plane fundamentally defines four mental conditions corresponding to four quadrants on the plane. The four mental conditions include a climax condition, a healing and relaxed condition, an anger and excited condition, and a disappointment and fatigue condition. The climax condition corresponds to a high mental activity degree and a pleasant feeling. The healing and relaxed condition corresponds to a low mental activity degree and a pleasant feeling. The anger and excited condition corresponds to a high mental activity degree and an unpleasant feeling. The disappointment and fatigue condition corresponds to a low mental activity degree and an unpleasant feeling. The feeling plane further defines a plurality of stages in each quadrant. The stages are classified in accordance with distance from the center of the feeling plane. In this embodiment, the feeling plane defines two stages. An area close to the center of the feeling plane is not categorized to the specific one of quadrant apparently, and shows a mean level of mental condition, i.e., a neutral mental condition. As a mental condition plotted on the feeling plane is more distanced from the neutral mental condition, the mental condition becomes to show a stronger emotion and/or desire specific for each quadrant. The mental point is determined in accordance with the detected mental condition. In detail, the mental point is defined based on the categories. In a strong climax condition (C), the mental point is set at +2. In a weak climax condition (C'), a strong healing and relaxed condition (D), a weak healing and relaxed condition (D'), and a neutral condition (N), the mental point is set at +1. In a weak disappointment and fatigue condition (D'), and a weak anger and excited condition (A'), the mental point is set at 0. In a strong disappointment and fatigue condition (D), and a strong anger and excited condition (A), the mental point is set at −1.

The degree J of the mental activity can be determined based on the heart rate H, or the blood flow velocity obtained by the heart echo measurement, or the breathing rate B obtained by the lung echo measurement. The user has a high mental activity when the user gets an angry, i.e., in an unpleasant direction, or feels an uplifting, i.e., in a pleasant direction. In such cases in the high mental activity, both the heart rate H and the breathing rate B show the tendency to increase. Conversely, when the user feels a fatigue or disappointment, i.e., in the unpleasant direction, or feels a cured leisurely and relaxing, i.e., in the pleasant direction, both the heart rate H and the breathing rate B show the tendency to decrease.

Figure 12:
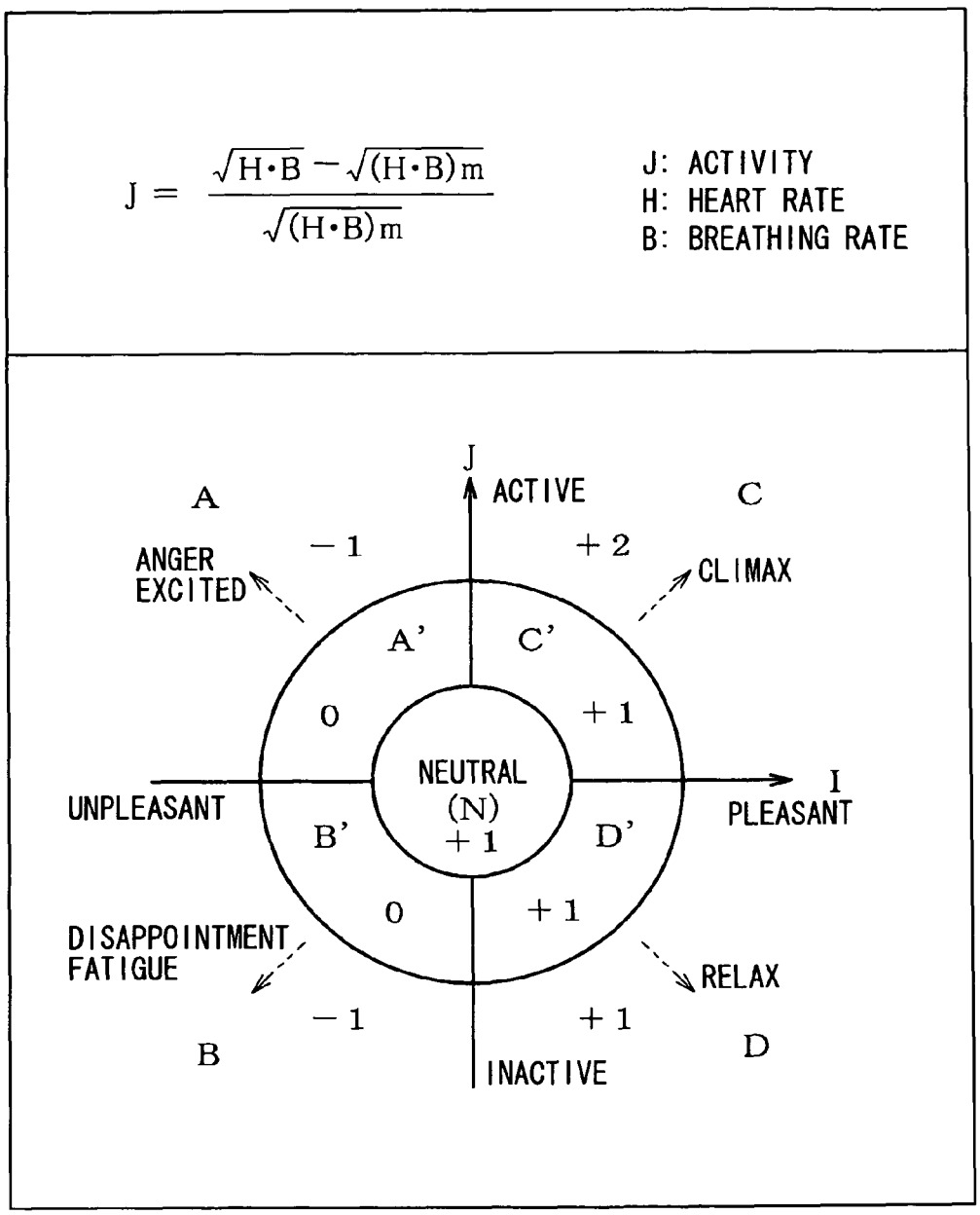
FIG. 12 is an explanatory diagram showing a relationship among parameters including a heart rate, a breathing rate and a blood flow velocity, a mental condition as an object to be determined, and a mental point.

In this embodiment, the degree J of the mental activity is defined to be zero "0" at the usual time, to be a positive value when it is higher than the usual, and to be a negative value when it is lower than the usual. For example, by measuring the heart rate and the breathing rate at the usual time beforehand, and assuming the measured values as Hm and Bm respectively, it is able to calculate by the following expressions, J=(H−Hm)/Hm or B=(B−Bm)/Bm. In this embodiment, as shown in FIG. 12, the degree J of the mental activity is calculated by using both the heart rate and the breathing rate. In detail, the degree J is calculated by using the square root of the product of the heart rate and the breathing rate.

Regarding the degree I of the pleasantness, in many cases, it is impossible to correctly determine whether the mental condition leans to the pleasant side or the unpleasant side only based on the heart rate and/or the breathing rate. Then, the apparatus separately determines the degree I of pleasant by monitoring the other living body parameters other than the echo measurement. For example, if the user gets nervous or angry and has a relatively high mental activity, the driver frequently changes a posture, but a change of the sight direction decreases conversely, i.e., so called a fixed eye condition.

In addition, the facial expression notably reflects and displays an expression of anger. The sight direction and the facial expression can be determined based on a face image captured by the face camera 521. The posture can be determined based on a posture measuring unit 600 in FIG. 3.

Figure 32:
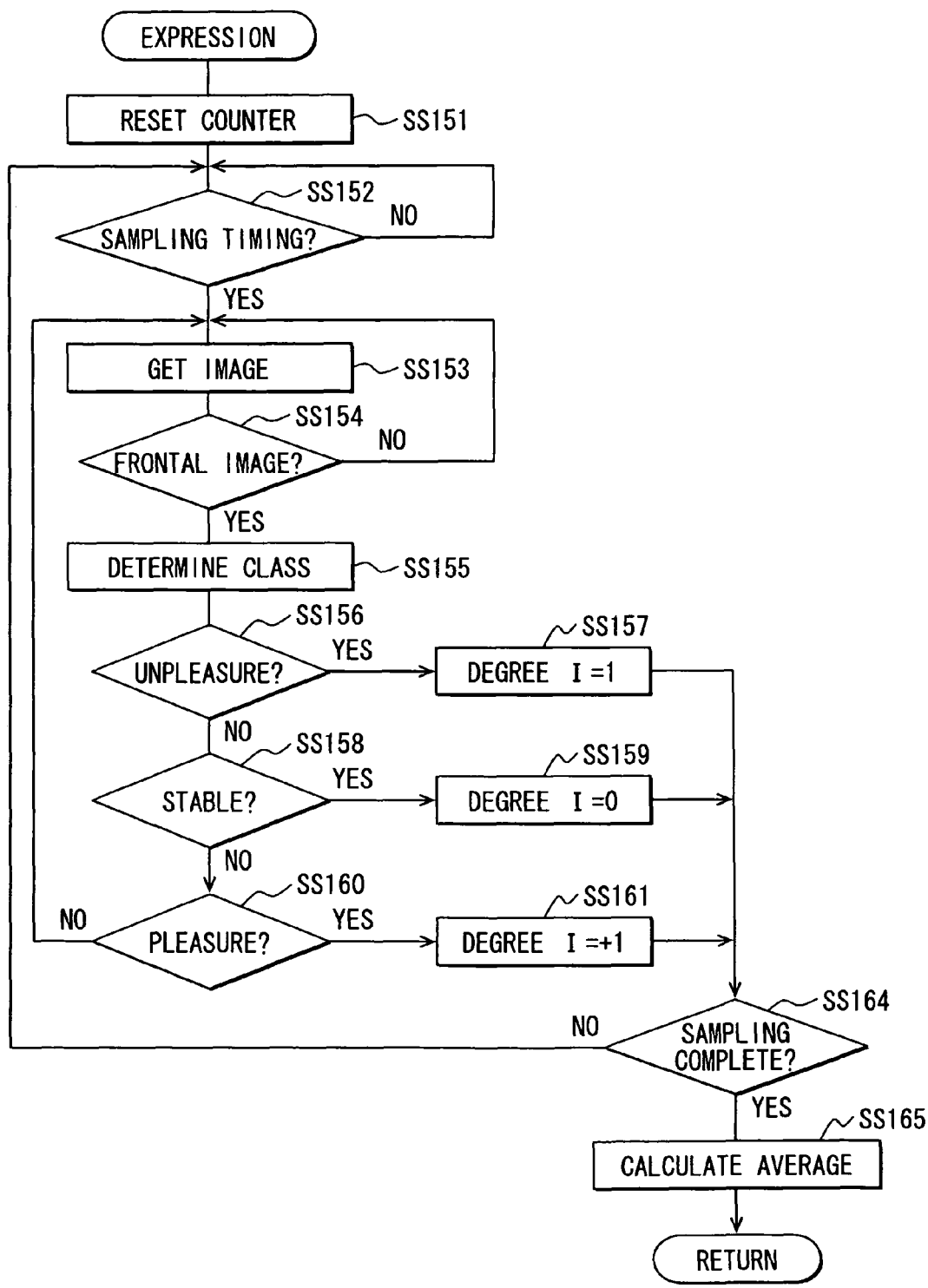
FIG. 32 is a flow chart showing an example of an expression change analysis processing flow for determining the degree of mental pleasant.

FIG. 32 shows an example of flowchart of expression change analysis processing. The counter N is reset in SS151. If a sampling timing comes in SS152, the process proceeds to SS153 and captures a face image. The capturing process for the face image is repeated until a frontal image capable for determining expression is obtained as shown in SS154 to SS153. If a frontal image is obtained, an expression classification is determined by comparing the frontal image with master images stored in the storage 535 in a one by one manner as shown in SS155. If the determined expression classification is an unpleasantness, the degree I is set to −1 in SS156 to SS157. If the determined expression classification is stable, the degree I is set to 0 in SS158 to SS159. If the determined expression classification is an unpleasantness, the degree I is set to +1 in SS160 to SS161. The above processing is repeated until the predetermined sampling period is expired as shown in SS164 to SS152. If the sampling period expires, the routine proceeds to SS165. In SS165, an average value I of the degree I is calculated. This process converts it into an integer.

Figure 33A:
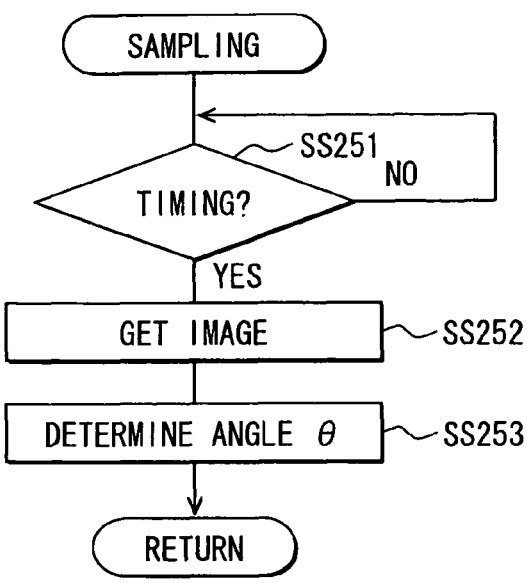
FIG. 33A is a flow chart showing an example of sight line direction analysis processing.
Figure 33B:
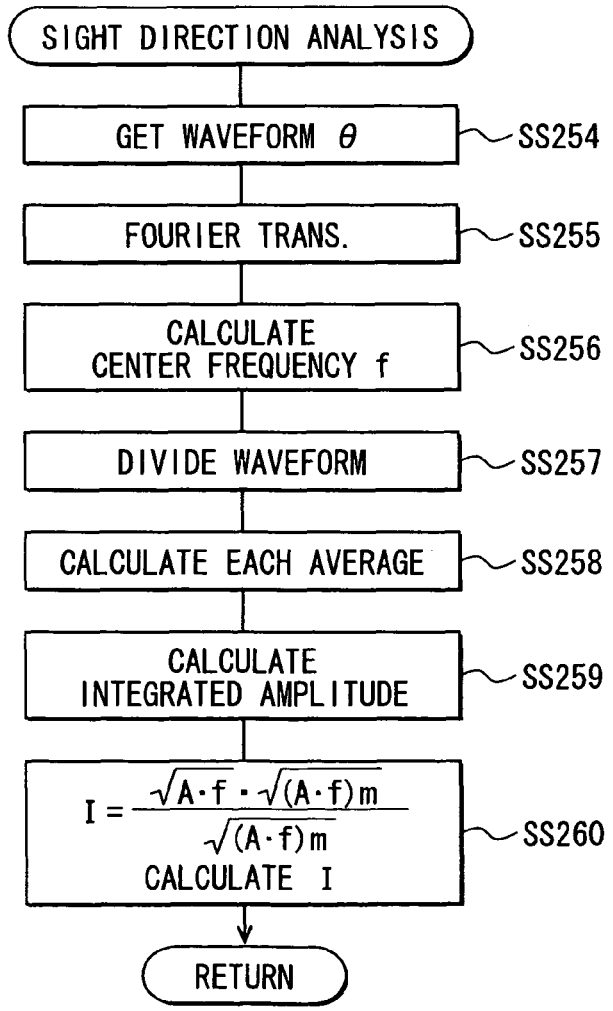
FIG. 33B is a flow chart showing an example of sight line direction analysis processing.

FIG. 33A and FIG. 33B show an example of the flow chart of sight direction angle waveform analysis processing. In a sampling routine, a face image is captured in SS252 when a sampling timing defined with a predetermined time interval comes. Then, an angle THETA of the sight direction is calculated in SS253 by locating a pupil and a face center in the face image, and calculating a deviation of the pupil from the frontal direction with respect to the face center. In an analysis routine, the values of the angle of the sight direction sampled in the latest predetermined period are acquired as a waveform in SS254. A frequency spectrum is calculated in SS255 by performing a well-known fast Fourier transform processing to the acquired waveform. A center frequency f, or a peak frequency on the spectrum is calculated in SS256. The apparatus divides the waveform into a plurality of sections in SS257. Then, average values of the sight direction for each section are calculated in SS258. Then, the apparatus determines a representative value A of a waveform amplitude in SS259. The representative value A is obtained as an averaged value of sectional integrated amplitudes. The sectional integrated amplitudes are calculated for each section by setting the average values of the sight direction as a center line for each section.

If a feeling leans to the unpleasantness side, an amplitude A of a sight direction change will become comparatively small, and a fluctuation, i.e., a frequency f, of the sight direction change becomes slow. Conversely, if the feeling leans to the pleasant side, the amplitude A of a sight direction change will become large, and the fluctuation, i.e., the frequency f, becomes active. In this embodiment, the degree I is defined to take a value zero "0" at the usual time, to take a positive value when it is higher than the usual, and to take a negative value when it is lower than the usual. For example, by measuring the amplitude A and the frequency f of the sight direction change at the usual time beforehand, and assuming the measured values as Am and fm respectively, it is able to calculate by the following expressions, $J=(A-Am)/Am$ or $J=(f-fm)/fm$. In this embodiment, the degree I of both the amplitude A and the frequency f is calculated in SS260.

Further, in the embodiment, the posture measurement unit 600 is configured to detect a posture change of a seating user, e.g., a driver, in a waveform detecting fashion based on detected outputs from the seating sensors 520A, 520B, and 520C embedded in the seat in a distributed fashion in the seating part and in the backrest part of the seat. The seating sensors all are provided by pressure sensors for detecting seating pressure respectively. More specifically, the seating sensor 520A that is arranged as a reference sensor is placed at the center of the back of the user facing to the front. Remaining sensors includes a left side sensor 520B placed on the left side from the center in an offset manner, and a right side sensor 520C placed on the right side from the center in an offset manner. A differential amplifier 603 calculates difference between an output from the reference sensor 520A and the right side sensor 520C. A differential amplifier 604 calculates difference between an output from the reference sensor 520A and the left side sensor 520B. Then, those outputs from the differential amplifiers 603 and 604 are supplied to a differential amplifier 605 for outputting a posture signal. The posture signal output Vout, i.e., referred to as a second biological parameter, takes substantially a reference value (e.g., zero volt) when the user is sitting toward front. The posture signal output Vout shifts to the negative side when the user shifts posture to the right, since an output from the right side sensor 520C increases and an output from the left side sensor 520B decreases. If the user shifts posture to the left, the sensors and the circuit functions opposite and the posture signal output Vout shifts to the positive side. In the illustrated circuit, both output from the right side sensors 520C in the seating part and the backrest part are added by an adder 601. Also, both output from the left side sensors 520B in the seating part and the backrest part are added by an adder 602. Alternatively, the circuit may be configured to supply a differential value between the outputs from the sensors in the seating part and the backrest part. In this case, it is possible to detect a shift of the user attitude as a greater collapse of the user posture, since the output from the sensor in the backrest part is decreased and the differential value increases when the user leans forward.

Figure 34:
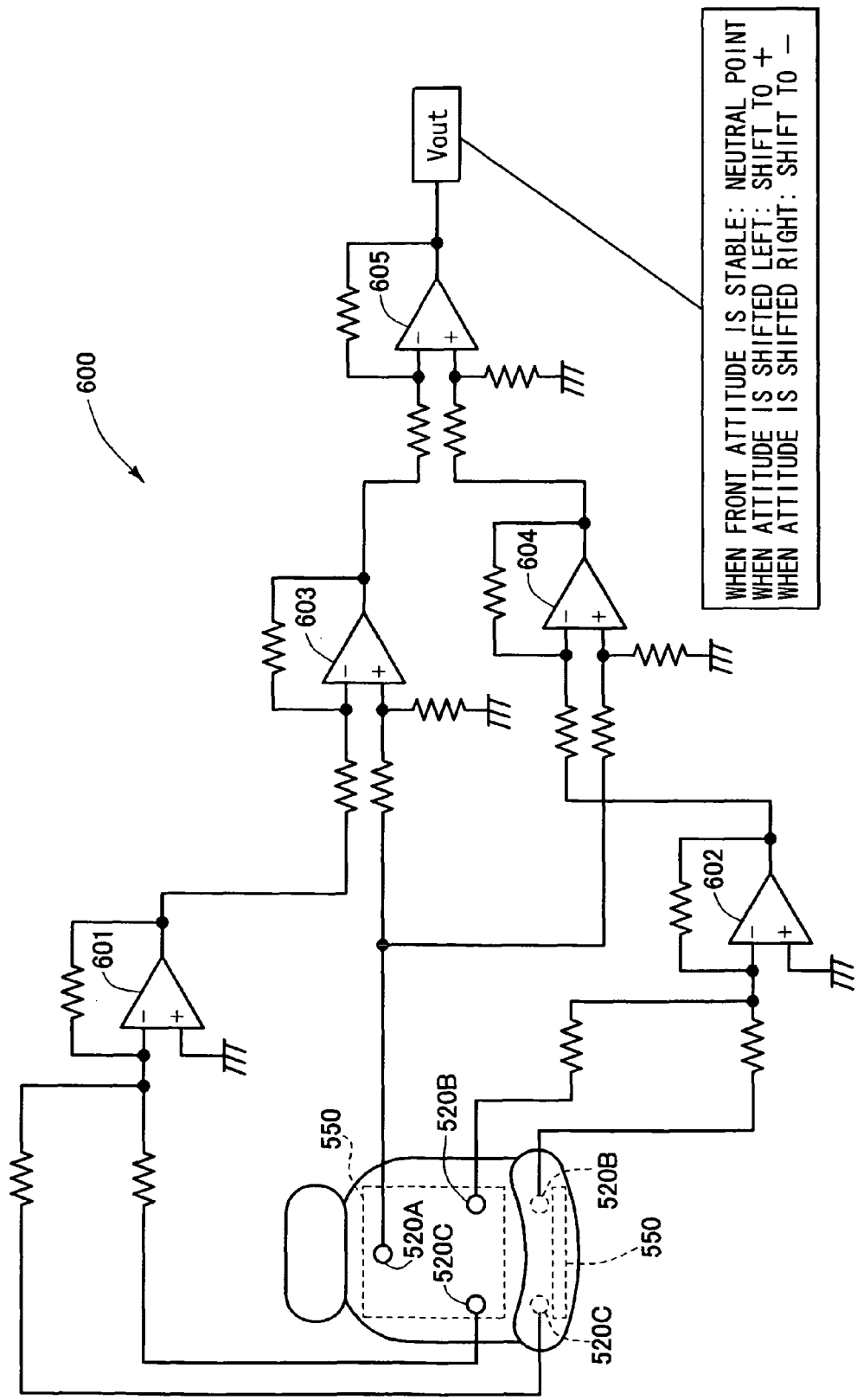
FIG. 34 is a circuit diagram showing an example of a posture measuring unit.
Figure 35A:
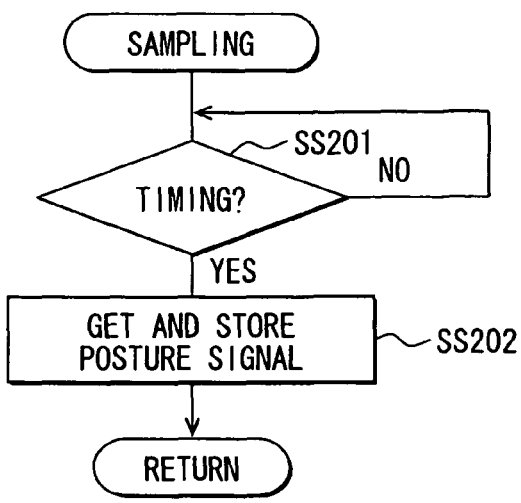
FIG. 35A is a flow chart showing an example of a posture change analysis processing flow for determining the degree of mental pleasant.
Figure 35B:
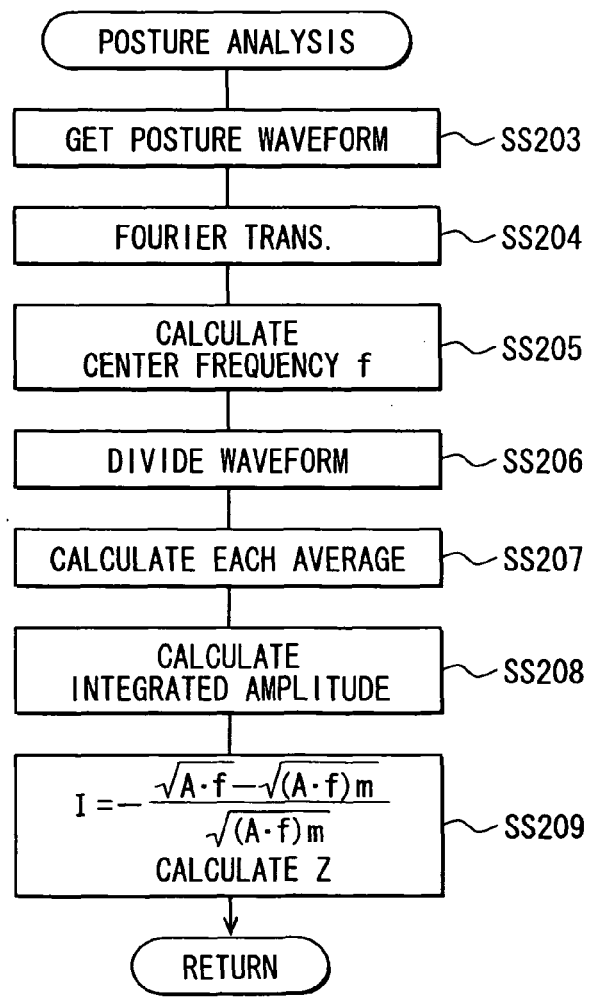
FIG. 35B is a flow chart showing an example of a posture change analysis processing flow for determining the degree of mental pleasant.

FIG. 35A and FIG. 35B show an example of the flow chart of posture waveform analysis processing. In a sampling routine, a waveform is recorded in SS201 and SS202 by sampling a posture signal (Vout) described before by using FIG. 34 when a sampling timing defined with a predetermined time interval comes. In an analysis routine, the values of the posture signal sampled in the latest predetermined period are acquired as a waveform in SS203. A frequency spectrum is calculated in SS204 by performing a well-known fast Fourier transform processing to the acquired waveform. A center frequency f, or a peak frequency on the spectrum is calculated in SS205. The apparatus divides the waveform into a plurality of sections in SS206. Then, average values of the posture signal for each sections are calculated in SS207. Then, the apparatus determines a representative value A of a waveform amplitude in SS259. The representative value A is obtained as an averaged value of sectional integrated amplitudes. The sectional integrated amplitudes are calculated for each section by setting the average values of the posture signal as a center line for each section.

Opposite to the case of the sight direction, if a feeling leans to the unpleasantness side, an amplitude A of a posture change will become comparatively large, and a fluctuation, i.e., a frequency f, of the posture change becomes frequent. Conversely, if the feeling leans to the pleasant side, the amplitude A of the posture change will become small, and the fluctuation, i.e., the frequency f, becomes mild. As mentioned before, the degree I of pleasantness is defined to take a value zero "0" at the usual time, to take a positive value when it is higher than the usual, and to take a negative value when it is lower than the usual. For example, by measuring the amplitude A and the frequency f of the posture change at the usual time beforehand, and assuming the measured values as Am and fm respectively, it is able to calculate by the following expressions, $J=(A-Am)/Am$ or $J=(f-fm)/fm$. In this embodiment, the degree I of both the amplitude A and the frequency f is calculated in SS209.

Although each of the degree I of pleasure obtainable by the three above-mentioned methods may be used solely, this embodiment uses an average value, e.g., geometric mean value, of the degree of pleasure obtained by several different methods in order to improve an accuracy of determination for the degree of pleasure. In addition to the above, for the purpose of determining the degree of pleasure, it is possible to reference a nonverbal gesture or a hand gesture, etc. which are appeared on the body according to a feeling.

The speech recognition unit 130, which provides a speech recognition means, performs processing which carries out the transliteration of the spoken language which a user inputs from the microphone 131 by a well-known available algorithm using the Hidden Markov Model. More specifically, as shown in FIG. 1, the character string obtained as a result of the speech recognition is processed and decomposed into words, by a well-known morphological-analysis technique, and is recognized in the decomposed words form.

The interest analysis software 109*b* in the flash memory 109 extracts keywords for determining a user's interest from an inputted content that was recognized by the speech recognition. A keyword dictionary 109*c* which covers a group of interest determining keywords beforehand selected for determining an interest is stored in the flash memory 109, i.e., a key word dictionary storage part. The speech recognition result indicative of decomposed words is compared with the keyword group registered in the key word dictionary 109*c* in a word by word manner. As a result, only the keyword covered by the keyword dictionary 109*c* is extracted selectively. In FIG. 1, examples of extracted keywords are indicated by double quotation marks " ".

Only keywords which are considered effective to narrow the service information contents are registered in the keyword dictionary 109*c*. For example, the registered keywords directly reflect information genres, e.g., a car accessory, an amusement, a meal, etc., classifications of goods or service, e.g., a tire, skiing, etc., seasons, proper nouns, e.g., a name of a place, a name of a person, a store name, etc., are registered. For example, in the above-mentioned conversation, the quoted words are registered as the keywords. Therefore, the apparatus can extract only the keywords which are marked with the double quotation marks by comparing the words provided by decompositing the above-mentioned conversation with the keyword dictionary 109*c*.

The keyword dictionary 109*c* accompanies a dictionary tool which functions as a keyword dictionary renewal means. The dictionary tool is performed periodically. The dictionary tool demands distribution of keyword update information containing a group of new keywords related to a season, fashion, or newest topics to a dictionary distribution server through the Internet 1170 or the other communication network, and updates the keyword dictionary 109*c* by the keyword update information acquired by receiving the distribution. In detail, the dictionary tool adds a new keyword if the keyword update information contains the new keyword, and contrary, deletes a specific keyword if the keyword update information contains a deletion command for the specific keyword. For example, some keywords only for a season are registered in the dictionary in a limited manner for a specific period corresponding to the season, and are deleted when the specific period expires. For example, "snow", "skiing", "stud-less" etc. are considered to be a keyword peculiar to winter, and has a specific period such as from November to April.

In parallel to an extraction of keywords, a mental condition when the keyword is spoken is monitored by the above-mentioned echo measurement at any time. Then, by executing the mental condition analysis software 109*e*, a value of the mental point corresponding to the mental condition is determined as shown in a lower part of FIG. 12, and is stored and accumulated in a keyword memory in the flash memory 109 in a form associated and linked with the extracted keyword and identification information of the user, e.g., a user name, who speaks the keyword. The keyword memory provides a memory means for the interest determining base data. The keyword memory also provides a base data accumulating means. In addition, subject in the vehicle changes every moment. Therefore, in order to exactly determine an interest object attracting attention among users now, the keyword memory is configured to accumulate only the keyword extracted within a latest predetermined period, and to delete the keyword accumulated for the predetermined period in an orderly fashion. The predetermined period may be defined as a certain period to the present time. The certain period is measured by the calendar clock 153, i.e., a time measuring means. For example, the certain period may be set within a range from 5 minutes to 60 minutes. Alternatively, the keyword memory may be configured as a FIFO memory, i.e., a first-in and first-out type memory, having a limited capacity. The memory may be managed to delete from the oldest one of the interest determining base data in an orderly manner when the memory runs a remaining capacity out due to a progression of data accumulation.

Figure 8:
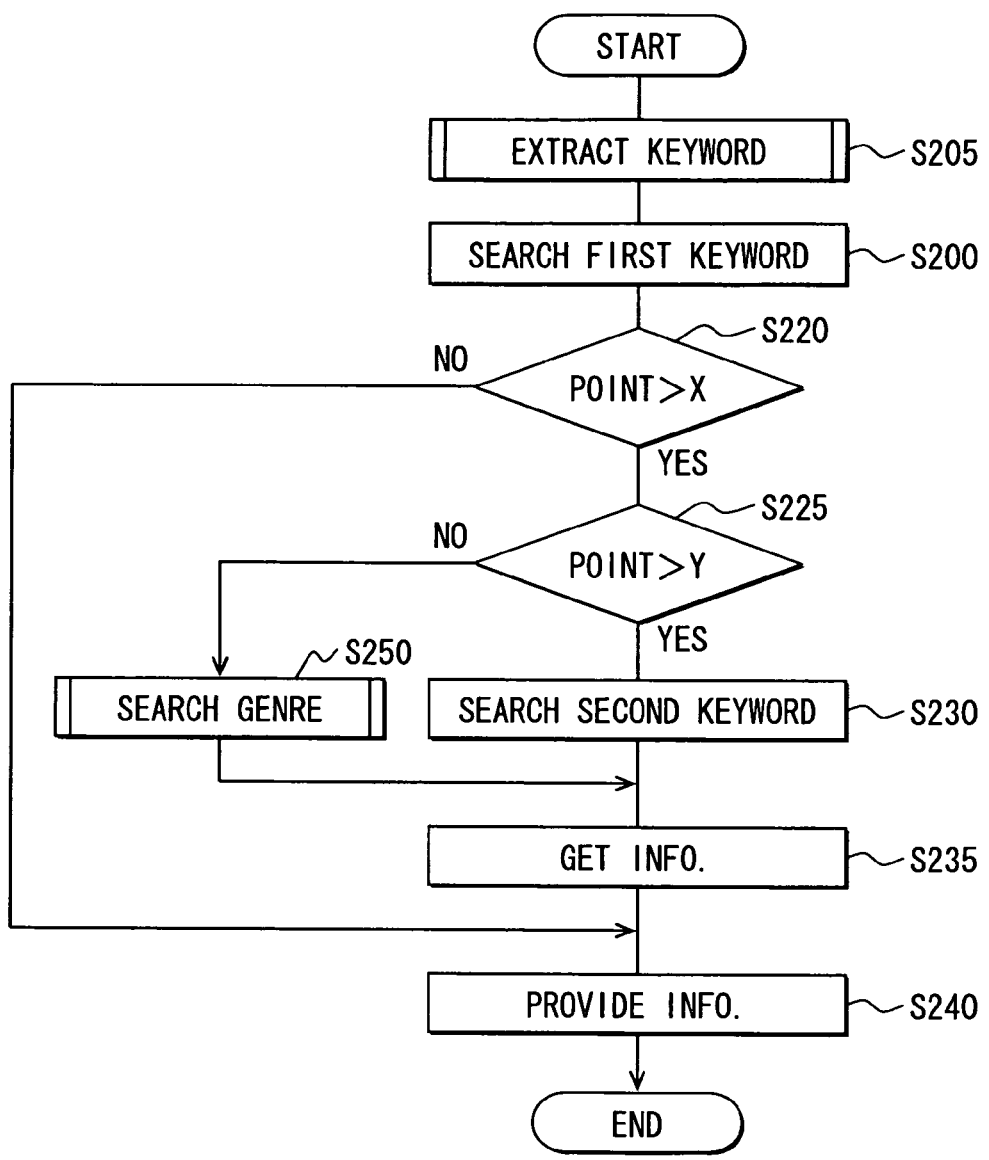
FIG. 8 is a flow chart showing a main processing flow.
Figure 9:
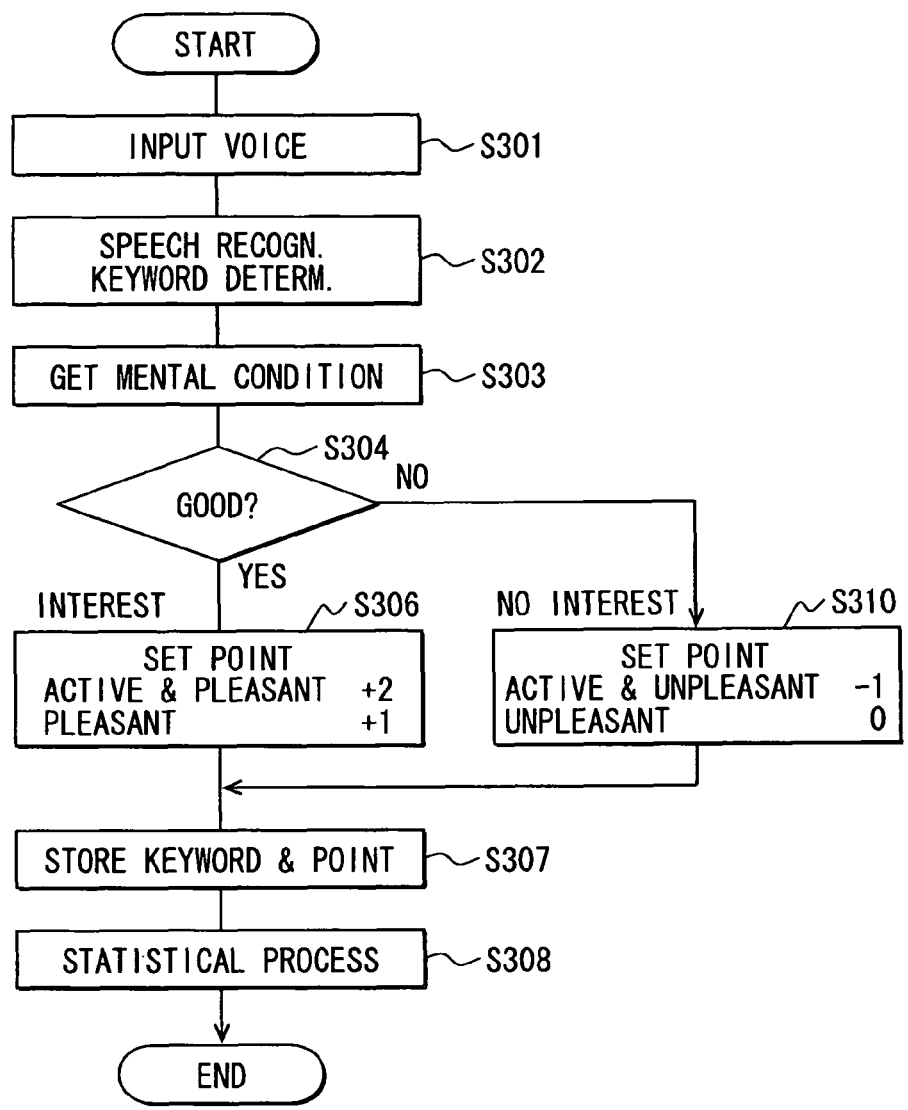
FIG. 9 is a flow chart showing a keyword extracting processing flow.

Hereafter, operation of the above-mentioned vehicle information providing apparatus 534 is explained. FIG. 8 shows a flow of main processing. Keyword extraction processing is first performed in S205. FIG. 9 shows details of the flow of S205. In a case that a user talks in the vehicle, the contents are picked up by the microphone 131 for every seat shown in FIG. 2 in S301. Then, conversation content is converted into a character string, and decomposed into words by the speech recognition. Then, extracting processing for keywords is carried out by looking up the keyword dictionary 109*c* as shown in FIG. 1 in S302. Next, in S303, the mental condition of the user who speaks the keyword is determined by the above-mentioned method of using the echo measuring unit 112.

Figure 10:
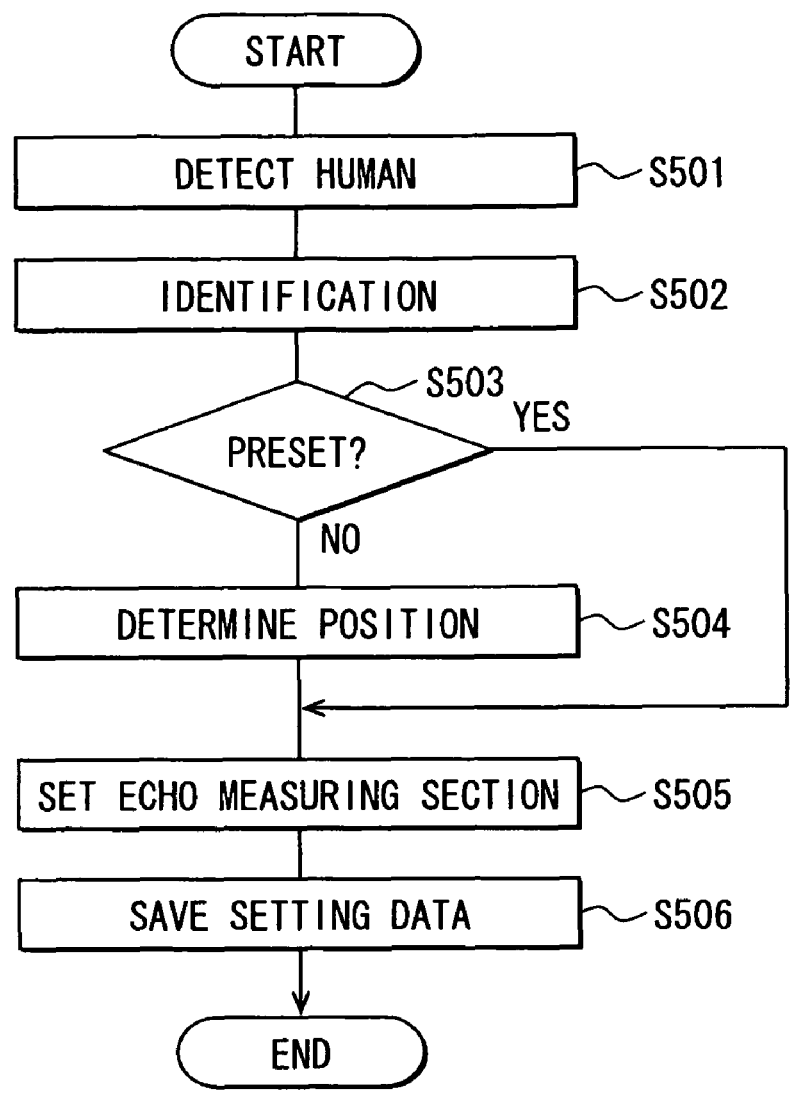
FIG. 10 is a first flow chart showing a setting processing flow of the echo measuring unit.
Figure 11:
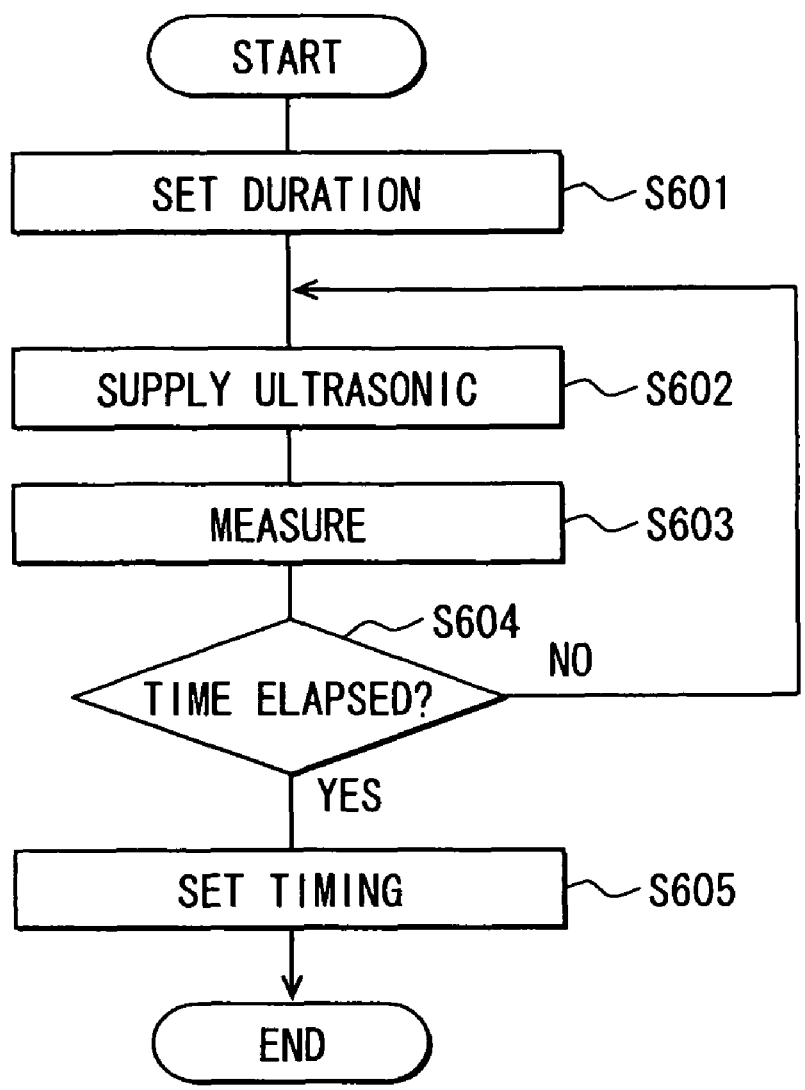
FIG. 11 is a first flow chart.

FIG. 10 and FIG. 11 show a flow of mental condition determining processing. As mentioned above, FIG. 10 shows processing which determines which is the one located in an optimal position among the prepared first echo measuring sections. First, it is determined whether a human, i.e., a user, is sitting on a seat or not by the seating sensor 520 in S501. Then, a personal identification is performed on the person sitting on the seat by capturing by the face camera 521 and matching in S502. After that, it is determined whether there is a preset data relating to an optimal position of the first echo measuring section for the identified user or not in S503. If no setting data is found, the routine proceeds to S504 and performs processing for determining the optimal position. If a preset data is found, the routine skips S504.

The location of the ultrasonic transmission part 1090 of the second echo measuring section is fixed in S504. In S504, further, a plurality of the ultrasonic transmission part 1070 of the first echo measuring sections are activated in an orderly manner by a switching operation of the switch 1030. In S504, further, the apparatus acquires the output of the adder 1060 as the differential waveform, and converts it into a frequency-time base waveform. Then, the apparatus determines the ultrasonic transmission part 1070 that has a maximum amplitude on the frequency-time base waveform, and saves it in the memory with the user name.

In S505, the location of the first echo measuring section corresponding to the identified user name is set up as a measuring condition. In S506, the measuring condition is saved. Then, the measuring flow shown in FIG. 11 is started. A duration time for applying an ultrasonic wave is set in S601. The applying time is considered sufficient if a time period that is equal to or longer than a one cycle period of the heart rate or the breathing rate for measured is obtained. For example, it may be set within a range from 2 to 5 seconds. Then, a switch 1030 shown in FIG. 4 is changed to activate the ultrasonic transmission part 1070 determined in S602. Then, an ultrasonic wave is generated. Consequently, an echo waveform is measured in S603. An elapsed time is judged in S604. In detail, it is judged whether a measuring time period determined in S601 is elapsed or not. If the measuring time is elapsed, a next timing for initiating the main processing shown in FIG. 9 is set in S605, and the routine is completed. For example, the next timing is set within a range from 1 to 60 seconds.

Returning to FIG. 9, a value of the mental point corresponding to the determined mental condition is acquired in S304, S306, and S310. In S307, the keyword is associated and linked with a user name and a mental point, and is memorized and accumulated in the keyword memory as interest determining base data. FIG. 13 shows an example of a first conversation with extracted keywords and obtained mental points. The extracted keywords are denoted by double quotation marks " ". The mental points obtained are shown in numbers on right side of the keywords by superscripts. FIG. 14 shows corresponding storage of contents of the keyword memory. By executing the interest analysis software 109a, the contents of storage in the keyword memory is converted into statistical data by calculating a totaled value, i.e., a total point, of the mental point as shown in FIG. 15.

Then, in the example of FIG. 8, the routine proceeds to S200, and searches a destination containing the keyword having the highest totaled value of the mental point on the destination data base 21d. The keyword having the highest totaled value of the mental point is called as the first keyword. It is apparent in FIG. 15, the applicable keywords are "snow" and "tire." In addition, the apparatus conducts an information retrieval on the Internet through a search engine site. A search starting keyword is predetermined. The speech recognition recognizes the search starting keyword when some one in the users speaks it, and obtains a trigger for starting a search. In FIG. 13, searching process is started in response to a detection of "search" which is the keyword spoken by TAKASHI.

In FIG. 13, if an attention is paid only to the occurrence frequency of the keyword, in addition to the keywords "snow", "tire", "stud-less" which are in the main subject, the occurrence frequency of "bus" is also high after them. However, it is apparent from a flow of the conversation, HITOMI who speaks "bus" first is unpleasantly telling the memory of hard bus tour in the year before last. Therefore, in response to detecting a mental condition with a high degree of unpleasantness within. B and A shown in FIG. 12, a negative value −1 is given to the mental point for the keyword "bus" spoken by HITOMI. Also in the utterance of TAKASHI responsive to the above, the keyword "bus" occurring twice take the mental point of zero "0" and −1. As a result, the keyword "but" has comparatively high occurrence frequency, i.e., 3 times, but has −2 of the totaled value of the mental point, therefore, is not adopted for a destination searching.

Returning to FIG. 8, in S220, the visit frequency for the searched destination is looked up with reference to the destination visit history, i.e., the destination history, on the output history data 21d in FIG. 9 stored in the HDD 121. If the visit frequency is less than a first threshold value X, e.g., X=2, in S235, the process promptly proceeds to S240. Then, the apparatus displays destinations matched on the monitor 110 in a listed manner and invites the user to perform a selection. On the other hand, when the visit frequency is equal to or more than the first threshold value X in S220, the process proceeds to S225. If the visit frequency is less than a first threshold value Y, e.g., Y=4, the process proceeds to S250. Here, extended retrieval processing is conducted in a form where destinations that does not include the keyword are placed as searching targets by using the classification, i.e., a sub classification code or a genre code, to which the hit destination belongs. Then, the apparatus displays the result on the monitor 110 in a listed manner and invites the user to perform a selection.

If the visit frequency is equal to or more than the first threshold value Y, it judges that the destination is obsolete and progresses to S230. Here, retrieval processing is conducted by expanding subjective destinations by an OR logic between the above-mentioned first keyword and a keyword called a second keyword which has the second high totaled value of the mental point. Then, the apparatus displays the result on the monitor 110 in a listed manner and invites the user to perform a selection. FIG. 16 shows an example of display in a listed form, which displays respective destination selection button 110B in a form where the past visit frequency can be discriminated. For example, the destination selection buttons 110B are classified by color according to visit frequency. A user can switch to the destination setting screen 122 shown in FIG. 17 by touching on a corresponding button on the touch panel 112. Then, a user can finalize a destination setting by touching on a finalizing button 122F, and start a guidance.

In a case that the contents file of the website acquired by the past access is memorized in the contents data 21u in the HDD 121, the contents file may be just read out from the HDD 121 and outputted to the monitor 110 without any access to the contents providing server 500. However, if the last access was held before a predetermined time, an output to the monitor 110 is performed based on an access to the contents providing server 500. In this case, an old contents file is renewed in an overwriting manner by a re-downloaded contents file.

Next, as shown in FIG. 16, it is possible that an appropriate destination selection can not performed because too many destinations equal to or more than the threshold valve may be searched by using the first keyword only. In this case, a narrowing process on the destination candidates can be performed by an AND logic with the second keyword. FIG. 16 shows an example of a destination list and selection buttons 110B on a display, in a case where "snow" is used as the second keyword, and "tire", "hot spring" and "skiing" are used as the second keywords.

Figure 18:
FIG. 18 is a plan view of a display showing a first example of display for contents of a website.

FIG. 17 shows an example of a destination setting screen 122 on a display, when one of tire shops is selected as a destination, in a case where a narrowing processing is performed by using "tire" as a second keyword. Since the website of the tire shop accompanies a shopping page, a link button to the shopping page is provided as an access button 122s. FIG. 18 shows a display image 122s of the shopping page.

Figure 19:
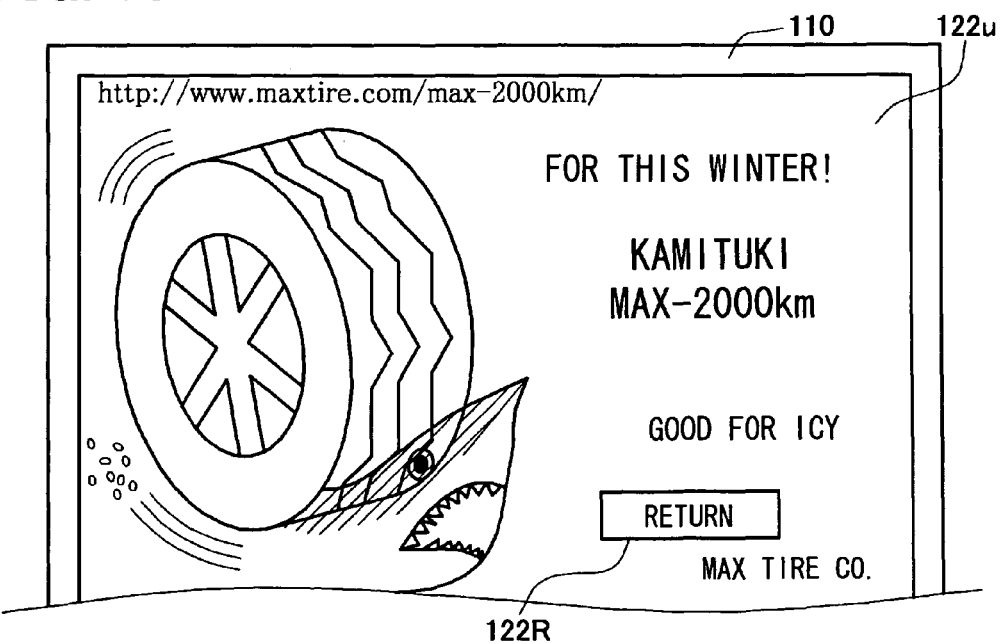
FIG. 19 is a plan view of a display showing a second example.

In addition, if an information service relating to an access record of the pertinent information in an external search website can be obtained from a third party during a narrowing process, the apparatus may be configured to additionally set and display a link button to the pertinent information obtainable website as an auxiliary access button 110E as shown in FIG. 16. For example, the apparatus transmits keywords "snow" and "tire" to a search website. Then, the search website conducts a website search for the goods, e.g., a stud-less tire, related to the transmitted keywords, and creates the statistical data which reflects the access frequency of the searched website. Then, the search website sends URL information of a website which shows the goods having the highest access frequency among the associated goods back to the vehicle information providing apparatus 534. The vehicle information providing apparatus 534 creates an auxiliary access button 110E in response to the above. FIG. 19 shows an image 122U displayed on the monitor 110 when the auxiliary access button 110E is executed.

Figure 21:
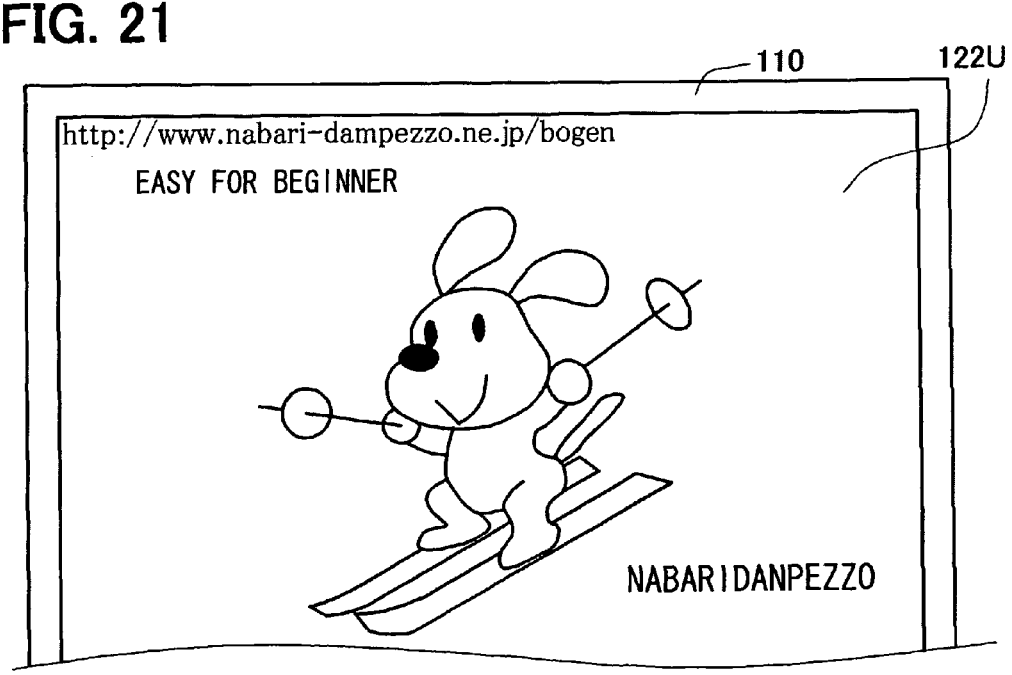
FIG. 21 is a plan view of a display showing a first example of display for contents of a website.

FIG. 20 shows an example of a display of a destination setting screen 122 when one of skiing areas is selected as a destination, in a case where narrowing processing is performed by using "skiing" as a second keyword. A link button for enabling a link to the website of the skiing area is prepared as the access button 122s. FIG. 21 shows an image 122U displayed on the monitor 110 when the access button 122s is executed.

Figure 22:
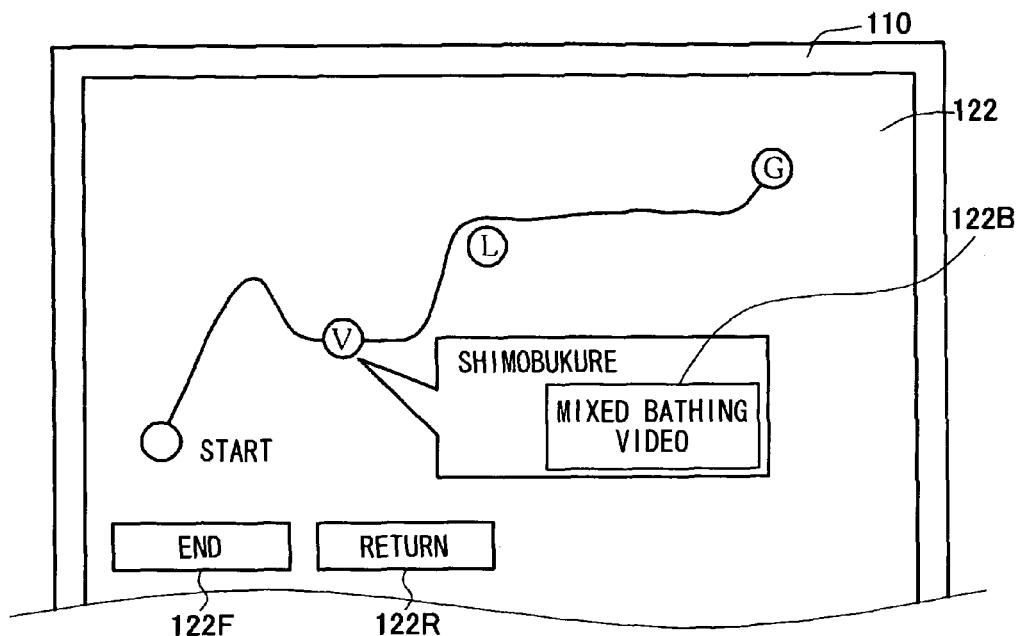
FIG. 22 is a plan view of a display showing a third display example of a destination setting screen in response to the search results of FIG. 16.
Figure 23:
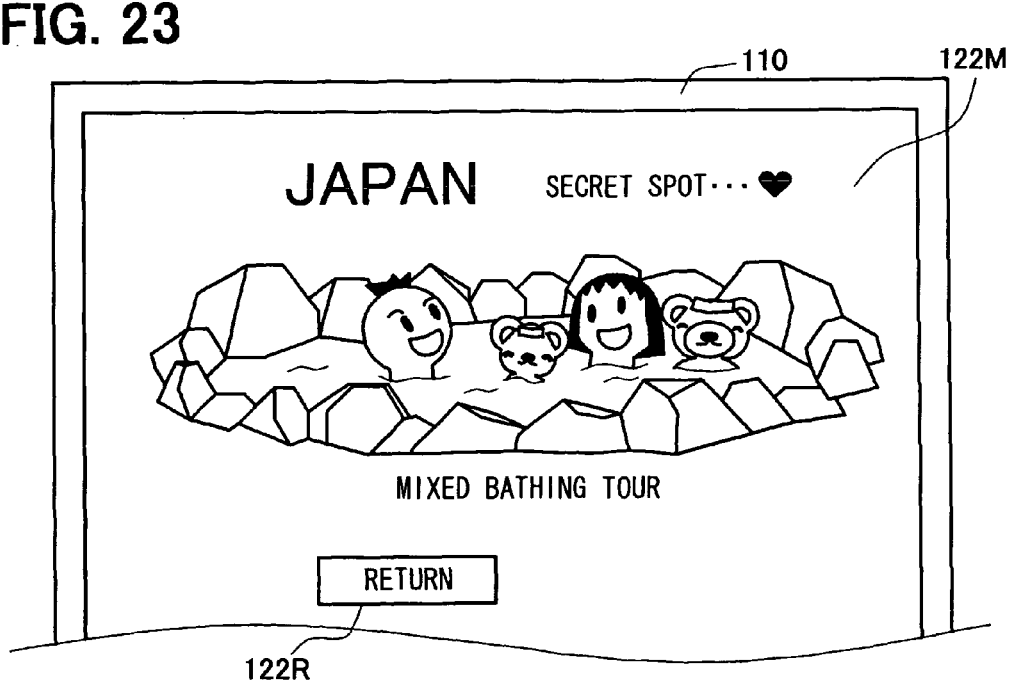
FIG. 23 is a plan view of a display showing a first example of display for contents of a website.

FIG. 22 shows an example of a display of a destination setting screen 122 when one of hot-spring resorts is selected as a destination, in a case where a narrowing processing is performed by using "hot spring" as a second keyword. Here, an access button 122B for enabling an access to a hot spring related image information memorized in the contents data 21u in the HDD 121 is provided. FIG. 23 shows an example of a display of an image 122M provided when the access button 122B is executed.

FIG. 24 shows an example of a second conversation. FIG. 25 shows corresponding contents of the storage of the keyword memory. FIG. 26 shows statistical data of a totaled value of the mental point for every keyword. In this example, by paying an attention to the occurrence frequency of the keywords, the most occurred keyword is the keyword "ITO" occurred 6 times, and the next occurred keywords are the keyword "non-toll road" occurred 3 times and the keyword "Mt. Fuji" occurred 3 times as shown in FIG. 25. The keyword "ITO" seems to be apparently adopted as an indispensable keyword in information searching. However, in closely evaluating the flow of the conversation of FIG. 24, ERIKA seems to get angry against spoken contents after the fifth line of SHOUGO who does not bear so negative feeling against "non-toll road", and ERIKA speaks conversation sentences including "non-toll road" while expressing a considerable anger. In this example, the mental point of "non-toll road" spoken by SHOGO is +1. The mental point of "non-toll road" spoken by ERIKA is −1. Therefore, zero "0" is obtained for the mental point of "non-toll road" which occurred twice but contributions cancel each other. In addition, SHOUGO flinches from the utterance of ERIKA, therefore, hesitatingly speaks the second "non-toll road" with the mental point of zero "0" under the influence of the stress. As a result, the keyword "non-tall road" has comparatively high occurrence frequency, i.e., 3 times, but has zero "0" of the totaled value of the mental point, therefore, is not adopted for a destination searching.

Figure 27:
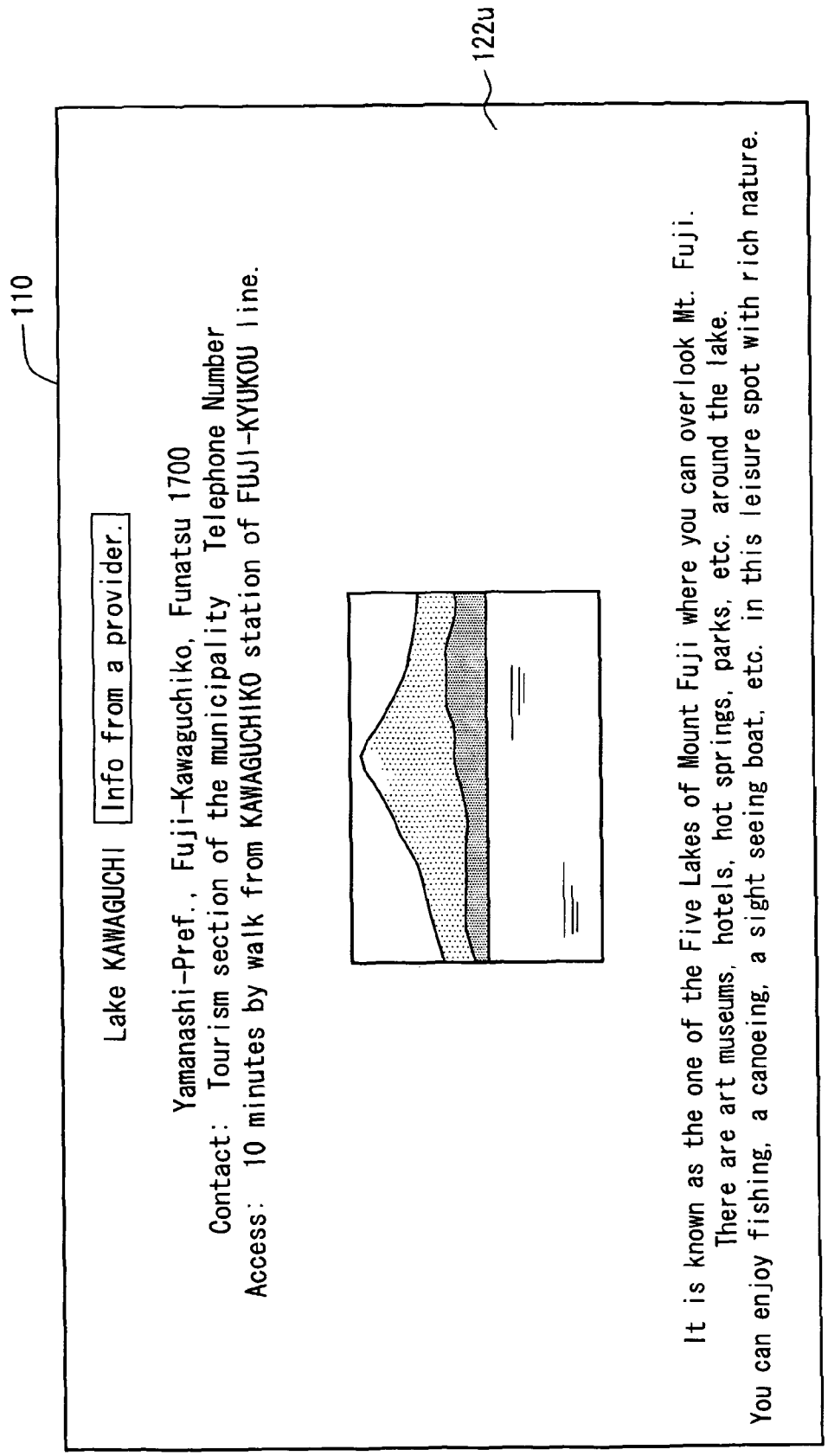
FIG. 27 is a plan view of a display showing an example of service information searched in response to the keyword extraction result of FIG. 26.

In addition, on the conversation context, the mental point of "ITO" closely connected with "non-toll road" takes +1 in the first utterance of YUKIO due to a mild feeling at a departure. Except for the above, but the mental point of "ITO" takes zero "0" or −1 in the later 5 times. For example, it takes zero "0" due to concerning a fatigue in the second utterance of YUKIO in response to an utterance of SHOUGO who speaks about getting out of toll road. For example, it takes −1 in the utterance of the enraged ERIKA. As a result, the totaled value of a mental point is set to −1, and it is not adopted for destination search processing. On the other hand, regarding the keyword "Mt. Fuji", ERIKA changes mind and is pleased, since SHOUGO suggests a short time trip. Therefore, a high mental point such as +2 is obtained for the keyword "Mt. Fuji" which ERIKA speaks at the very last. Therefore, the keyword "Mt. Fuji" merely has 3 times of the occurrence frequency, but takes +4 of the totaled value of the mental point that is the maximum as shown in FIG. 26. As a result, by using a word "search" spoken by SHOUGO as a trigger, the apparatus actually adopts "Mt. Fuji" as the first keyword and "Fuji Five Lakes" as the second keyword. Consequently, the guidance information shown in FIG. 27 is searched on the Internet and outputted.

Thus, the mental point which was prepared for every extracted keyword shows the mental condition that was expressed to the keyword by a group of users. In other words, the mental condition corresponds to a good feeling or a bad feeling of a group of users. In this embodiment, it is provided that a means for determining whether a user or a group of users expresses a good feeling to the extracted keyword or not based on the mental point indicative of the mental condition. In another way of explanation, the apparatus selects a favorable keyword from the plurality of keywords. The favorable keyword is a keyword which a user or a group of users expresses a good feeling. The apparatus collects service information only based on a favorable keyword. As a result, the apparatus can provide the information relating to the keyword which the user expresses a good feeling. On the other hand, it is possible to avoid providing the information relating to the keyword which the user does not express a good feeling.

FIG. 28 shows an example of a third conversation. FIG. 29 shows a statistical data of a totaled value of the mental point for every keyword. In this example, a conversation is held at a time within a meal time, and shows a situation where the users have a conversation about a noodle shop in the news of a television and where the users have a lively conversation about a "roast pork" which is especially the centers of the news. In detail, since a plurality of lively talking members call a "roast pork" repeatedly, the totaled value of the mental point reaches to +10 which is defined as a threshold value by virtue of the keyword "roast pork" alone as shown in FIG. 29. The apparatus automatically supplies a trigger command to a search engine in response to the above, and performs search processing by using a "roast pork" as a first keyword and using a "TENKOMORI" which is a name of the restaurant as a second keyword.

Figure 30:
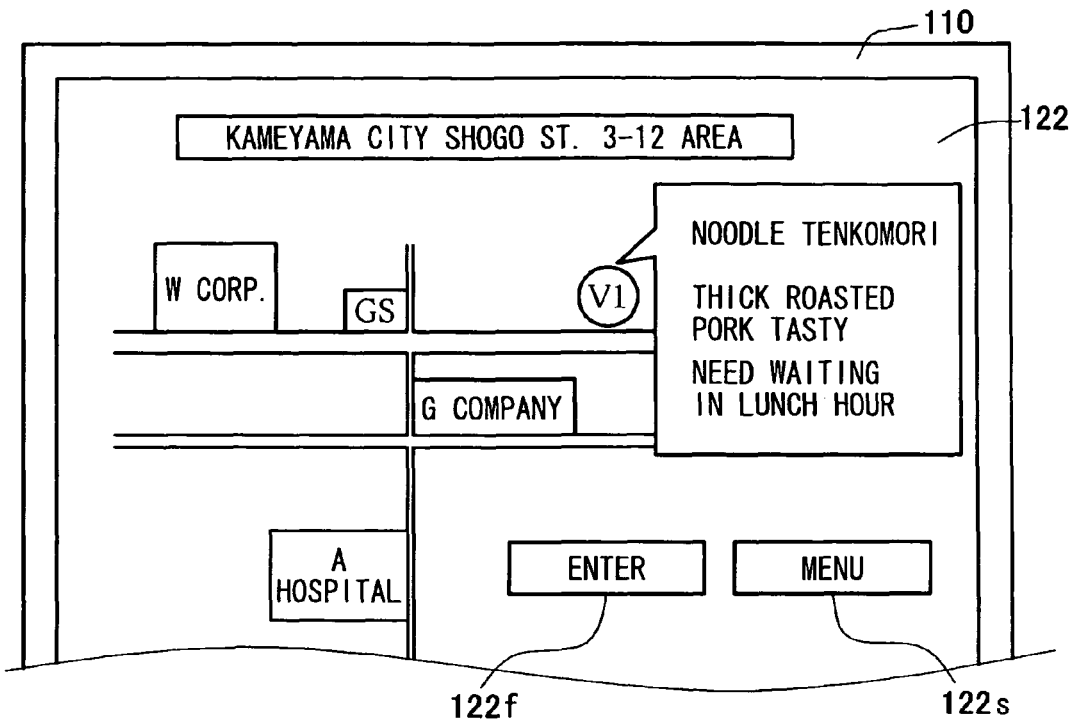
FIG. 30 is a plan view of a display showing the first example output of service information searched in response to the keyword extraction result of FIG. 29.
Figure 31:
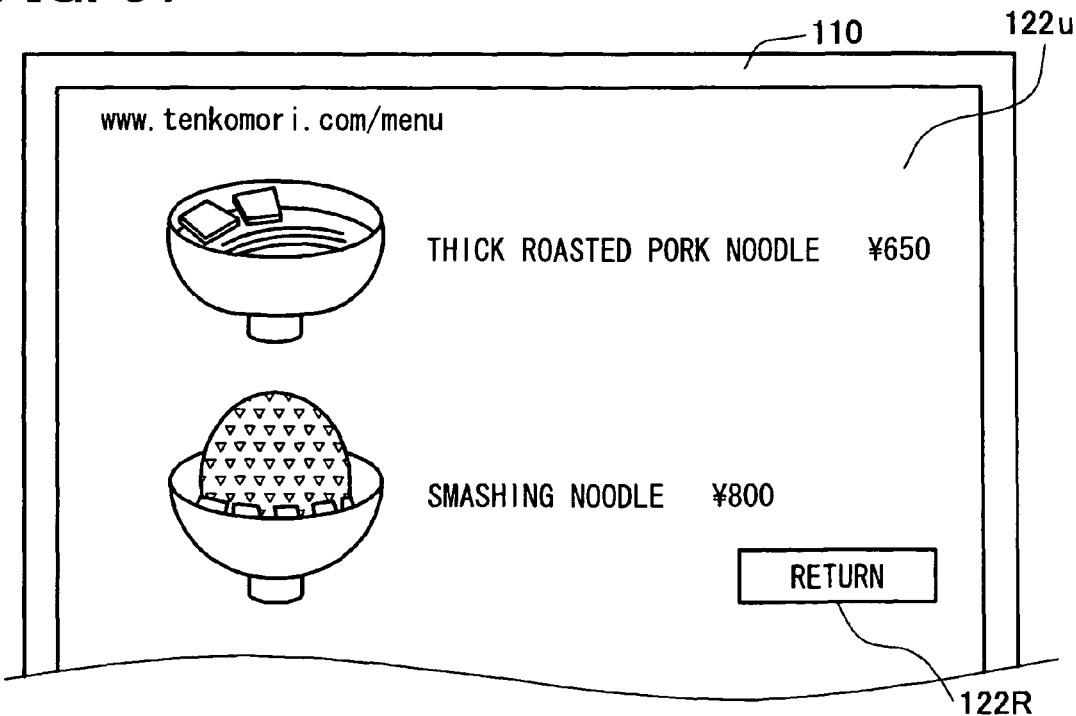
FIG. 31 is a plan view of a display showing a second example.

FIG. 30 shows a result of search output of the destination. In a case that there is other service information relevant to the destination, an access button 122s associated to the service information is additionally displayed. The apparatus can output the service information in response to an, execution of the access button 122s. For example, in a case that the service information is contents of the Internet website, the access button 122s is formed as a link button to the website. In this example, the destinations are restaurants, therefore, if it is required to show a menu of the restaurants, the access button 122s is attached with an URL link to a menu showing page which is a part of the contents. By execution of this access button 122s, a wireless access is made from the vehicle information providing apparatus 534 to the contents providing server 500, i.e., the information service server, of the website. Then, a menu page is displayed on the monitor 110 as shown in FIG. 31.

Although the present invention has been fully described in connection with the preferred embodiments thereof with reference to the accompanying drawings, it is to be noted that various changes and modifications will become apparent to those skilled in the art. Such changes and modifications are to be understood as being within the scope of the present invention as defined by the appended claims.

What is claimed is:

1. An apparatus for providing information for vehicle comprising:
    conversation inputting means for inputting contents of a conversation of a user in a vehicle;
    speech-recognition means for recognizing the contents of the conversation by using a speech recognition;
    keyword extracting means for extracting a keyword to be used for a user's interest determination from the contents of the conversation recognized by the speech recognition;
    mental condition detecting means for detecting a mental condition of a user when the contents of the conversation is inputted by detecting at least one of a heart rate, a breathing rate and a blood flow velocity of the user, the mental condition being shifted to either a good feeling state or a poor feeling state in speaking;
    mental condition quality determining means for determining quality of the detected mental condition,
    base data accumulating means for handling the result of mental condition quality determination as mental condition information that is linked with the keyword, and for accumulating a pair of the result of the mental condition quality determination and the linked keyword as interest determining base data;
    user interest information extracting means for extracting a keyword reflecting a user's present interest based on the mental condition information as user interest information from the interest determining base data;
    service information collecting means for collecting service information to be served to the user by searching based on the keyword extracted as the user interest information; and
    service information output means to output the collected service information in a form of an image, audio, or those combination, wherein:
    the mental condition quality determining means includes mental point converting means for converting the mental condition detected by the mental condition detecting means into a mental point which is defined to have a larger numerical value as the mental condition becomes better;
    the base data accumulating means accumulates the interest determining base data which is provided by handling the mental point as the mental condition information to be associated and linked with the keyword; and
    the user interest information extracting means analyzes a frequency of occurrence of the keyword accumulated in the base data accumulating means, and gives a higher ranking of priority for searching the service information to the keyword which has a higher occurrence frequency and better result of the mental condition quality determination, wherein
    the base data accumulating means accumulates only the keyword extracted within a latest predetermined period, and deletes the keyword accumulated for the predetermined period.

2. The apparatus for providing information for vehicle in claim 1, wherein the service information output means is configured to output the service information in response to acquiring a predetermined service trigger information.

3. The apparatus for providing information for vehicle in claim 1, wherein the service information output means is configured to include a car-navigation system, and wherein the information collection means searches and collects destination information which suits the user interest information as the service information on the car-navigation system.

4. The apparatus for providing information for vehicle in claim 1, wherein the service information output means includes a wireless access device to website on the Internet, and wherein the service information collecting means searches and collects website information on the Internet as the service information which suits the user interest information.

5. The apparatus for providing information for vehicle in claim 1, wherein the service information collecting means selects a keyword which the user has a good feeling based on the mental condition detected by the mental condition detecting means, and collects the service information only based on the selected keyword.

6. An apparatus for providing information for vehicle comprising:
    conversation inputting means for inputting contents of a conversation of a user in a vehicle;
    speech-recognition means for recognizing the contents of the conversation by using a; speech recognition;
    keyword extracting means for extracting a keyword to be used for a user's interest determination from the contents of the conversation recognized by the speech recognition;
    mental condition detecting means for detecting a mental condition of a user when the contents of the conversation is inputted by detecting at least one of a heart rate, a breathing rate and a blood flow velocity of the user, the mental condition being shifted to either a good feeling state or a poor feeling state in speaking;
    mental condition quality determining means for determining quality of the detected mental condition,
    base data accumulating means for handling the result of mental condition quality determination as mental condition information that is linked with the keyword, and for accumulating a pair of the result of the mental condition quality determination and the linked keyword as interest determining base data;
    user interest information extracting means for extracting a keyword reflecting a user's present interest based on the mental condition information as user interest information from the interest determining base data;
    service information collecting means for collecting service information to be served to the user by searching based on the keyword extracted as the user interest information; and
    service information means to output the collected service information in a form of an image, audio, or those combination, wherein:
    the mental condition quality determining means includes mental point converting means for converting the mental condition detected by the mental condition detecting means into a mental point which is defined to have a larger numerical value as the mental condition becomes better;
    the base data accumulating means accumulates the interest determining base data which is provided by handling the mental point as the mental condition information to be associated and linked with the keyword; and the user interest information extracting means analyzes a frequency of occurrence of the keyword accumulated in the base data accumulating means, and gives a higher ranking of priority for searching the service information to the keyword which has a higher occurrence frequency and better result of the mental condition quality determination, wherein the base data accumulating means accumulates only the keyword extracted within a latest predetermined period, and deletes the keyword accumulated for the predetermined period in an orderly fashion, wherein the user interest information extracting means is configured so that the keyword which is linked with the result of the mental condition quality determination poorer than a predetermined level in the interest determining base data is not adopted for searching the service information in the service information collecting means.

7. The apparatus for providing information for vehicle in claim 6, wherein the user interest information extracting means sums the mental point for each classification of the keywords accumulated in the base data accumulating means, and gives the higher ranking of priority for searching the service information in the service information collecting means to the keyword as the totaled point of the mental point for the keyword becomes higher.

8. The apparatus for providing information for vehicle in claim 7, herein the mental point converting means sets a value of zero or negative to the mental point linked with the keyword that is contained in a conversation when the mental condition is poorer than a predetermined level.

9. The apparatus for providing information for vehicle in claim 8, wherein the user interest information extracting means withdraws the keyword having zero or negative totaled point of the mental point from the searching of the service information in the service information collecting means.

10. The apparatus for providing information for vehicle in claim 7, further comprising service trigger information output means for outputting service trigger information for providing information when the totaled point of the mental point exceeds a threshold value defined beforehand about the extracted keyword, wherein the service information output means outputs the service information by acquiring the service trigger information.

11. An apparatus for providing information for vehicle comprising:

conversation inputting means for inputting contents of a conversation of a user in a vehicle;

speech-recognition means for recognizing the contents of the conversation by using a speech recognition;

keyword extracting means for extracting a keyword to be used for a user's interest determination from the contents of the conversation recognized by the speech recognition;

mental condition detecting means for detecting a mental condition of a user when the contents of the conversation is inputted by detecting at least one of a heart rate, a breathing rate and a blood flow velocity of the user, the mental condition being shifted to either a good feeling state or a poor feeling state in speaking;

mental condition quality determining means for a determining quality of the detected mental condition, base data accumulating means for handling the result of mental condition quality determination as mental condition information that is linked with the keyword, and for accumulating a pair of the result of the mental condition quality determination and the linked keyword as interest determining base data;

user interest information extracting means for extracting a keyword reflecting a user's present interest based on the mental condition information as user interest information from the interest determining base data;

service information collecting means for collecting service information to be served to the user by searching based on the keyword extracted as the user interest information; and service information output means to output the collected service information in a form of an image, audio, or those combination, wherein:

the mental condition quality determining means includes mental point converting means for converting the mental condition detected by the mental condition detecting means into a mental point which is defined to have a larger numerical value as the mental condition becomes better;

the base data accumulating means accumulates the interest determining base data which is provided by handling the mental point as the mental condition information to be associated am linked with the keyword; and the user interest information extracting means analyzes a frequency occurrence of the keyword accumulated in the base data accumulating means, and gives a higher ranking of priority for searching the service information the keyword which has a higher occurrence frequency and better result of the mental condition quality determination, wherein the base data accumulating means accumulates only the keyword extracted within a latest predetermined period, and deletes the keyword accumulated for the predetermined period in an orderly fashion, wherein the mental condition detecting means includes an echo measuring unit which performs an echo measurement on the heart or the lung of the user who is sitting on the seat of the vehicle for detecting at least one of the heart rate, the breathing rate and the blood flow velocity of the user, and detects the mental condition based on the echo measurement result.

12. The apparatus for providing information for vehicle in claim 11, wherein the echo measuring unit has an ultrasonic supplying section and an ultrasonic receiving section both embedded in a seat back portion of a seat to perform the echo measurement of the user.

13. The apparatus for providing information for vehicle in claim 12, wherein the mental condition detecting means includes: a first echo measuring section including an ultrasonic transmission part and a reflection ultrasonic receiving part both made for a first measuring target including one of a heart and a lung, a second echo measuring section including an ultrasonic transmission part and a reflection ultrasonic receiving part both made for a second measuring target that includes human body portions other than the first measuring target, and a differential calculation section which calculates and outputs a differential waveform between an output waveform from the reflection ultrasonic receiving part of the first echo measuring section and an output waveform from the reflection ultrasonic receiving part of the second echo measuring section, and wherein the mental condition detecting means determines at least one of the heart rate, the breathing rate, and the blood flow velocity based on the differential waveform.

14. The apparatus for providing information for vehicle in claim 11, wherein the mental condition detecting means further includes a pleasant degree detecting means, disposed separately from the echo measuring unit, for determining a pleasant degree that is determined separately by a living body parameter other than the echo measurement, wherein the mental condition detecting means determines a degree of the mental activity based on the result of the measurement of the echo measuring unit, and wherein the mental condition detecting means determines the mental condition based on a combination of the degree of the mental activity and the pleasant degree.

15. The apparatus for providing information for vehicle in claim 14, wherein the pleasant degree detecting means detects the pleasant degree based on at least one of an expression, a sight direction, and a posture of the user.

* * * * *